(12) United States Patent
Shelton, IV

(10) Patent No.: US 9,226,760 B2
(45) Date of Patent: Jan. 5, 2016

(54) LAPAROSCOPIC DEVICES WITH FLEXIBLE ACTUATION MECHANISMS

(75) Inventor: Frederick E. Shelton, IV, Hillsboro, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 922 days.

(21) Appl. No.: 12/775,819

(22) Filed: May 7, 2010

(65) Prior Publication Data

US 2011/0276084 A1 Nov. 10, 2011

(51) Int. Cl.
*A61B 17/00* (2006.01)
*A61B 17/29* (2006.01)

(52) U.S. Cl.
CPC .......... *A61B 17/29* (2013.01); *A61B 2017/2902* (2013.01); *A61B 2017/2903* (2013.01)

(58) Field of Classification Search
CPC ........... A61B 17/29; A61B 2017/2902; A61B 2017/2903; A61B 2017/2912; A61B 2017/2927; A61B 2017/2929
USPC .......... 606/145, 148, 210, 205–209; 600/200, 600/204, 206, 249; 277/175.1, 176.1
See application file for complete search history.

(56) References Cited

U.S. PATENT DOCUMENTS

| | | |
|---|---|---|
| 2,129,391 A | 9/1938 | Wappler |
| 2,765,930 A | 10/1956 | Greer et al. |
| 3,402,710 A | 9/1968 | Paleschuck |
| 3,503,396 A | 3/1970 | Pierie et al. |
| 3,654,965 A | 4/1972 | Gramain |
| 4,041,931 A | 8/1977 | Elliott et al. |
| 4,048,987 A | 9/1977 | Hurson |
| 4,112,932 A | 9/1978 | Chiulli |
| 4,120,302 A | 10/1978 | Ziegler |
| 4,203,430 A | 5/1980 | Takahashi |
| 4,306,545 A | 12/1981 | Ivan et al. |
| 4,373,532 A | 2/1983 | Hill et al. |
| 4,402,683 A | 9/1983 | Kopman |
| 4,417,888 A | 11/1983 | Cosentino et al. |
| 4,559,947 A | 12/1985 | Renger et al. |
| 4,608,977 A | 9/1986 | Brown |

(Continued)

FOREIGN PATENT DOCUMENTS

| | | |
|---|---|---|
| DE | 43 00 307 A1 | 7/1994 |
| DE | 43 24 254 C1 | 1/1995 |

(Continued)

OTHER PUBLICATIONS

U.S. Appl. No. 12/399,473, filed Mar. 6, 2009 entitled Methods and Devices for Providing Access Into a Body Cavity.

(Continued)

*Primary Examiner* — Jonathan W Miles
*Assistant Examiner* — Kendra Obu

(57) ABSTRACT

Methods and devices are provided for performing minimally invasive surgical procedures. In one embodiment, a surgical device is provided that includes an elongate shaft having an end effector at a distal end thereof. The end effector can be configured to be movable between a first configuration in which the end effector is longitudinally aligned with or linear relative to the shaft and a second configuration in which the end effector is articulated at an angle beyond 45 degrees relative to the shaft. With the end effector in the first configuration or in the second configuration, the device can be configured to allow selective actuation of the end effector.

16 Claims, 9 Drawing Sheets

(56) References Cited

U.S. PATENT DOCUMENTS

| | | |
|---|---|---|
| 4,669,473 A | 6/1987 | Richards et al. |
| 4,821,719 A | 4/1989 | Fogarty |
| 4,831,070 A | 5/1989 | McInally et al. |
| 4,880,015 A | 11/1989 | Nierman |
| 5,020,514 A | 6/1991 | Heckele |
| 5,027,800 A | 7/1991 | Rowland |
| 5,058,603 A | 10/1991 | Doi et al. |
| 5,141,498 A | 8/1992 | Christian |
| 5,183,471 A | 2/1993 | Wilk |
| 5,197,955 A | 3/1993 | Stephens et al. |
| 5,201,742 A | 4/1993 | Hasson |
| 5,207,213 A | 5/1993 | Auhll et al. |
| 5,209,737 A | 5/1993 | Ritchart et al. |
| 5,209,741 A | 5/1993 | Spaeth |
| 5,209,747 A | 5/1993 | Knoepfler |
| 5,269,772 A | 12/1993 | Wilk |
| 5,275,614 A | 1/1994 | Haber et al. |
| 5,284,128 A * | 2/1994 | Hart ............... 600/208 |
| 5,308,336 A | 5/1994 | Hart et al. |
| 5,312,023 A | 5/1994 | Green et al. |
| 5,329,923 A | 7/1994 | Lundquist |
| 5,330,437 A | 7/1994 | Durman |
| 5,330,502 A | 7/1994 | Hassler et al. |
| 5,342,396 A | 8/1994 | Cook |
| 5,345,927 A | 9/1994 | Bonutti |
| 5,350,391 A | 9/1994 | Iacovelli |
| 5,360,428 A | 11/1994 | Hutchinson, Jr. |
| 5,362,294 A | 11/1994 | Seitzinger |
| 5,366,478 A | 11/1994 | Brinkerhoff et al. |
| 5,368,597 A | 11/1994 | Pagedas |
| 5,374,277 A | 12/1994 | Hassler |
| 5,381,943 A | 1/1995 | Allen et al. |
| 5,383,888 A | 1/1995 | Zvenyatsky et al. |
| 5,385,553 A | 1/1995 | Hart et al. |
| 5,385,560 A | 1/1995 | Wulf |
| 5,391,154 A | 2/1995 | Young |
| 5,398,617 A | 3/1995 | Deandrea |
| 5,403,342 A | 4/1995 | Tovey et al. |
| 5,417,203 A | 5/1995 | Tovey et al. |
| 5,419,339 A * | 5/1995 | Palmer ............... 600/564 |
| 5,441,483 A | 8/1995 | Avitall |
| 5,443,452 A | 8/1995 | Hart et al. |
| 5,443,484 A | 8/1995 | Kirsch et al. |
| 5,445,648 A | 8/1995 | Cook |
| 5,456,684 A | 10/1995 | Schmidt et al. |
| 5,480,410 A | 1/1996 | Cuschieri et al. |
| 5,489,256 A | 2/1996 | Adair |
| 5,489,290 A | 2/1996 | Furnish |
| 5,501,653 A | 3/1996 | Chin |
| 5,514,157 A | 5/1996 | Nicholas et al. |
| 5,520,609 A | 5/1996 | Moll et al. |
| 5,520,678 A | 5/1996 | Heckele et al. |
| 5,545,123 A | 8/1996 | Ortiz et al. |
| 5,545,179 A | 8/1996 | Williamson, IV |
| 5,547,458 A | 8/1996 | Ortiz et al. |
| 5,549,637 A | 8/1996 | Crainich |
| 5,569,205 A | 10/1996 | Hart et al. |
| 5,569,254 A | 10/1996 | Carlson et al. |
| 5,571,090 A | 11/1996 | Sherts |
| 5,571,129 A * | 11/1996 | Porter ............... 606/170 |
| 5,573,520 A | 11/1996 | Schwartz et al. |
| 5,578,048 A | 11/1996 | Pasqualucci et al. |
| 5,582,577 A | 12/1996 | Lund et al. |
| 5,582,617 A | 12/1996 | Klieman et al. |
| 5,584,850 A | 12/1996 | Hart et al. |
| 5,586,977 A | 12/1996 | Dorsey, III |
| 5,591,182 A | 1/1997 | Johnson |
| 5,595,193 A | 1/1997 | Walus et al. |
| 5,607,450 A | 3/1997 | Zvenyatsky et al. |
| 5,609,601 A | 3/1997 | Kolesa et al. |
| 5,618,291 A | 4/1997 | Thompson et al. |
| 5,618,294 A | 4/1997 | Aust et al. |
| 5,624,381 A | 4/1997 | Kieturakis |
| 5,626,608 A | 5/1997 | Cuny et al. |
| 5,630,831 A | 5/1997 | Lahr |
| 5,632,432 A | 5/1997 | Schulze et al. |
| 5,632,734 A * | 5/1997 | Galel et al. ............... 604/524 |
| 5,634,882 A | 6/1997 | Gagner |
| 5,634,883 A | 6/1997 | Chin et al. |
| 5,634,911 A | 6/1997 | Hermann et al. |
| 5,634,937 A | 6/1997 | Mollenauer et al. |
| 5,636,645 A | 6/1997 | Ou |
| 5,640,977 A | 6/1997 | Leahy et al. |
| 5,643,283 A | 7/1997 | Younker |
| 5,643,301 A | 7/1997 | Mollenauer |
| 5,647,372 A | 7/1997 | Tovey et al. |
| 5,653,705 A | 8/1997 | de la Torre et al. |
| 5,665,093 A | 9/1997 | Atkins et al. |
| 5,667,527 A | 9/1997 | Cook |
| 5,672,168 A | 9/1997 | de la Torre et al. |
| 5,676,146 A | 10/1997 | Scarborough |
| 5,676,657 A | 10/1997 | Yoon |
| 5,681,324 A | 10/1997 | Kammerer et al. |
| 5,695,448 A | 12/1997 | Kimura et al. |
| 5,700,275 A | 12/1997 | Bell et al. |
| 5,704,534 A | 1/1998 | Huitema et al. |
| 5,713,919 A | 2/1998 | Lahr |
| 5,716,327 A | 2/1998 | Warner et al. |
| 5,716,407 A | 2/1998 | Knapp et al. |
| 5,728,121 A | 3/1998 | Bimbo et al. |
| 5,735,289 A | 4/1998 | Pfeffer et al. |
| 5,743,456 A | 4/1998 | Jones et al. |
| 5,743,851 A | 4/1998 | Moll et al. |
| 5,766,205 A | 6/1998 | Zvenyatsky et al. |
| 5,772,654 A | 6/1998 | Leyva |
| 5,782,812 A | 7/1998 | Hart et al. |
| 5,782,859 A | 7/1998 | Nicholas et al. |
| 5,792,165 A | 8/1998 | Klieman et al. |
| 5,797,959 A | 8/1998 | Castro et al. |
| 5,803,919 A | 9/1998 | Hart et al. |
| 5,813,409 A | 9/1998 | Leahy et al. |
| 5,814,058 A | 9/1998 | Carlson et al. |
| 5,816,257 A | 10/1998 | Chin |
| 5,827,319 A | 10/1998 | Carlson et al. |
| 5,827,323 A | 10/1998 | Klieman et al. |
| 5,833,692 A * | 11/1998 | Cesarini et al. ............... 606/79 |
| 5,836,960 A | 11/1998 | Kolesa et al. |
| 5,840,078 A | 11/1998 | Yerys |
| 5,853,395 A | 12/1998 | Crook et al. |
| 5,865,807 A | 2/1999 | Blake, III |
| 5,872,859 A | 2/1999 | Gur et al. |
| 5,876,447 A | 3/1999 | Arnett |
| 5,891,013 A | 4/1999 | Thompson |
| 5,893,878 A | 4/1999 | Pierce |
| 5,906,577 A | 5/1999 | Beane et al. |
| 5,921,956 A | 7/1999 | Grinberg et al. |
| 5,941,890 A | 8/1999 | Voegele et al. |
| 5,947,922 A | 9/1999 | MacLeod |
| 5,957,913 A | 9/1999 | de la Torre et al. |
| 5,971,995 A | 10/1999 | Rousseau |
| 5,977,431 A | 11/1999 | Knapp et al. |
| 5,990,382 A | 11/1999 | Fox |
| 6,007,561 A | 12/1999 | Bourque et al. |
| 6,024,708 A | 2/2000 | Bales et al. |
| 6,024,736 A | 2/2000 | de la Torre et al. |
| 6,027,522 A | 2/2000 | Palmer |
| 6,033,428 A | 3/2000 | Sardella |
| RE36,702 E | 5/2000 | Green et al. |
| 6,074,419 A | 6/2000 | Healy et al. |
| 6,077,287 A * | 6/2000 | Taylor et al. ............... 606/170 |
| 6,077,288 A | 6/2000 | Shimomura et al. |
| 6,086,603 A | 7/2000 | Termin et al. |
| 6,093,141 A | 7/2000 | Mosseri et al. |
| 6,110,154 A | 8/2000 | Shimomura et al. |
| 6,110,182 A | 8/2000 | Mowlai-Ashtiani |
| 6,120,513 A | 9/2000 | Bailey et al. |
| 6,123,689 A | 9/2000 | To et al. |
| 6,126,671 A | 10/2000 | Richards et al. |
| 6,132,385 A | 10/2000 | Vain |
| 6,149,642 A | 11/2000 | Gerhart et al. |
| 6,156,045 A | 12/2000 | Ulbrich et al. |
| 6,156,184 A | 12/2000 | Antonucci et al. |
| 6,159,200 A | 12/2000 | Verdura et al. |
| 6,162,196 A | 12/2000 | Hart et al. |

(56) References Cited

U.S. PATENT DOCUMENTS

| | | | |
|---|---|---|---|
| 6,162,208 A | 12/2000 | Hipps | |
| 6,165,184 A | 12/2000 | Verdura et al. | |
| 6,171,282 B1 | 1/2001 | Ragsdale | |
| 6,197,034 B1 | 3/2001 | Gvozdic et al. | |
| 6,217,555 B1 | 4/2001 | Hart et al. | |
| 6,220,248 B1 | 4/2001 | Voegele et al. | |
| 6,228,055 B1 | 5/2001 | Foerster et al. | |
| 6,245,011 B1 | 6/2001 | Dudda et al. | |
| 6,245,052 B1 | 6/2001 | Orth et al. | |
| 6,248,062 B1 | 6/2001 | Adler et al. | |
| 6,258,069 B1 | 7/2001 | Carpentier et al. | |
| 6,258,102 B1 | 7/2001 | Pagedas | |
| 6,261,302 B1 | 7/2001 | Voegele et al. | |
| 6,264,599 B1 | 7/2001 | Slater et al. | |
| 6,290,705 B1 | 9/2001 | Chan et al. | |
| 6,293,966 B1 | 9/2001 | Frantzen | |
| 6,315,770 B1 | 11/2001 | de la Torre et al. | |
| 6,319,246 B1 | 11/2001 | de la Torre et al. | |
| 6,347,940 B1 | 2/2002 | Gordils et al. | |
| 6,348,034 B1 | 2/2002 | Thompson | |
| 6,352,503 B1 | 3/2002 | Matsui et al. | |
| 6,400,979 B1 | 6/2002 | Stoianovici et al. | |
| 6,402,687 B1 | 6/2002 | Ouchi | |
| 6,425,903 B1 | 7/2002 | Voegele | |
| 6,443,960 B1 | 9/2002 | Brabrand et al. | |
| 6,447,443 B1 | 9/2002 | Keogh et al. | |
| 6,447,489 B1 | 9/2002 | Peterson | |
| 6,454,783 B1 | 9/2002 | Piskun | |
| 6,456,184 B1 | 9/2002 | Vu et al. | |
| 6,458,077 B1 | 10/2002 | Boebel et al. | |
| 6,471,714 B1 | 10/2002 | Kim | |
| 6,485,467 B1 | 11/2002 | Crook et al. | |
| 6,494,211 B1 | 12/2002 | Boyd et al. | |
| 6,551,270 B1 | 4/2003 | Bimbo et al. | |
| 6,551,282 B1 | 4/2003 | Exline et al. | |
| 6,578,577 B2 | 6/2003 | Bonadio et al. | |
| 6,579,304 B1 | 6/2003 | Hart et al. | |
| 6,589,167 B1 | 7/2003 | Shimomura et al. | |
| 6,605,063 B2 | 8/2003 | Bousquet | |
| 6,613,068 B2 | 9/2003 | Ouchi | |
| 6,623,426 B2 | 9/2003 | Bonadio et al. | |
| 6,634,883 B2 | 10/2003 | Ranalli | |
| RE38,335 E * | 11/2003 | Aust et al. | 606/170 |
| 6,663,641 B1 | 12/2003 | Kovac et al. | |
| 6,665,554 B1 | 12/2003 | Charles et al. | |
| 6,666,854 B1 | 12/2003 | Lange et al. | |
| 6,669,674 B1 | 12/2003 | Macoviak et al. | |
| 6,673,092 B1 | 1/2004 | Bacher | |
| 6,689,122 B2 * | 2/2004 | Yamamoto | 606/1 |
| 6,706,033 B1 | 3/2004 | Martinez et al. | |
| 6,706,050 B1 | 3/2004 | Giannadakis | |
| 6,725,083 B1 | 4/2004 | Burbank et al. | |
| 6,764,473 B2 | 7/2004 | Morton | |
| 6,766,186 B1 | 7/2004 | Hoyns et al. | |
| 6,807,965 B1 | 10/2004 | Hickle | |
| 6,810,880 B1 | 11/2004 | Jennings, Jr. et al. | |
| 6,818,007 B1 | 11/2004 | Dampney et al. | |
| 6,821,247 B2 | 11/2004 | Vierra et al. | |
| 6,846,287 B2 | 1/2005 | Bonadio et al. | |
| 6,872,433 B2 * | 3/2005 | Seward et al. | 428/36.9 |
| 6,908,430 B2 | 6/2005 | Caldwell et al. | |
| 6,913,613 B2 | 7/2005 | Schwarz et al. | |
| 6,936,061 B2 | 8/2005 | Sasaki | |
| 6,939,296 B2 | 9/2005 | Ewers et al. | |
| 6,945,932 B1 | 9/2005 | Caldwell et al. | |
| 6,966,876 B2 | 11/2005 | Irion et al. | |
| 6,972,026 B1 | 12/2005 | Caldwell et al. | |
| 6,994,712 B1 | 2/2006 | Fisher et al. | |
| 7,008,377 B2 | 3/2006 | Beane et al. | |
| 7,014,628 B2 | 3/2006 | Bousquet | |
| 7,021,173 B2 | 4/2006 | Stoianovici et al. | |
| 7,047,063 B2 | 5/2006 | Burbank et al. | |
| 7,052,454 B2 | 5/2006 | Taylor | |
| 7,083,576 B2 | 8/2006 | Zarins et al. | |
| 7,083,626 B2 | 8/2006 | Hart et al. | |
| 7,087,071 B2 | 8/2006 | Nicholas et al. | |
| 7,118,528 B1 | 10/2006 | Piskun | |
| 7,147,650 B2 | 12/2006 | Lee | |
| 7,163,510 B2 | 1/2007 | Kahle et al. | |
| 7,201,734 B2 | 4/2007 | Hickle | |
| 7,208,005 B2 | 4/2007 | Frecker et al. | |
| 7,214,185 B1 | 5/2007 | Rosney et al. | |
| 7,247,154 B2 | 7/2007 | Hickle | |
| 7,311,661 B2 | 12/2007 | Heinrich | |
| 7,331,661 B2 | 2/2008 | Silverbrook et al. | |
| 7,331,750 B2 | 2/2008 | Merz et al. | |
| 7,338,473 B2 | 3/2008 | Campbell et al. | |
| 7,344,547 B2 | 3/2008 | Piskun | |
| 7,347,862 B2 | 3/2008 | Layer | |
| 7,416,533 B2 | 8/2008 | Gellman et al. | |
| 7,615,005 B2 | 11/2009 | Stefanchik et al. | |
| 7,691,095 B2 | 4/2010 | Bednarek et al. | |
| 7,909,220 B2 | 3/2011 | Viola | |
| 7,985,239 B2 * | 7/2011 | Suzuki | 606/206 |
| 7,988,699 B2 | 8/2011 | Martz et al. | |
| 8,083,667 B2 | 12/2011 | Cooper et al. | |
| 8,562,592 B2 | 10/2013 | Conlon et al. | |
| 2001/0034528 A1 | 10/2001 | Foerster et al. | |
| 2001/0053510 A1 | 12/2001 | Ranalli | |
| 2002/0007112 A1 | 1/2002 | Rupp et al. | |
| 2002/0026201 A1 | 2/2002 | Foerster et al. | |
| 2002/0103434 A1 | 8/2002 | Swanbom | |
| 2002/0156432 A1 | 10/2002 | Racenet et al. | |
| 2002/0156497 A1 | 10/2002 | Nagase et al. | |
| 2002/0173805 A1 | 11/2002 | Matsuno et al. | |
| 2002/0193815 A1 | 12/2002 | Foerster et al. | |
| 2003/0028179 A1 | 2/2003 | Piskun | |
| 2003/0028207 A1 | 2/2003 | Lang et al. | |
| 2003/0073882 A1 | 4/2003 | Smid et al. | |
| 2003/0100814 A1 | 5/2003 | Kindlein | |
| 2003/0109898 A1 | 6/2003 | Schwarz et al. | |
| 2003/0113540 A1 | 6/2003 | Anderson et al. | |
| 2003/0114838 A1 | 6/2003 | O'Neill et al. | |
| 2003/0120285 A1 | 6/2003 | Kortenbach | |
| 2003/0135204 A1 * | 7/2003 | Lee et al. | 606/1 |
| 2003/0139756 A1 | 7/2003 | Brustad | |
| 2003/0206860 A1 | 11/2003 | Bleyer et al. | |
| 2003/0208207 A1 | 11/2003 | Layer | |
| 2003/0225420 A1 | 12/2003 | Wardle | |
| 2003/0229338 A1 | 12/2003 | Irion et al. | |
| 2003/0236549 A1 | 12/2003 | Bonadio et al. | |
| 2004/0015185 A1 | 1/2004 | Ewers et al. | |
| 2004/0023161 A1 | 2/2004 | Yamaguchi et al. | |
| 2004/0024304 A1 | 2/2004 | Foerster et al. | |
| 2004/0068291 A1 | 4/2004 | Suzuki | |
| 2004/0106942 A1 | 6/2004 | Taylor et al. | |
| 2004/0106986 A1 | 6/2004 | Andersson et al. | |
| 2004/0138525 A1 | 7/2004 | Saadat et al. | |
| 2004/0138528 A1 | 7/2004 | Richter et al. | |
| 2004/0147933 A1 | 7/2004 | McGovern | |
| 2004/0167545 A1 | 8/2004 | Sadler et al. | |
| 2004/0193146 A1 * | 9/2004 | Lee et al. | 606/1 |
| 2004/0193212 A1 | 9/2004 | Taniguchi et al. | |
| 2004/0215063 A1 | 10/2004 | Bonadio et al. | |
| 2004/0225323 A1 | 11/2004 | Nagase et al. | |
| 2004/0230160 A1 | 11/2004 | Blanco | |
| 2004/0230161 A1 | 11/2004 | Zeiner | |
| 2004/0243108 A1 | 12/2004 | Suzuki | |
| 2004/0254426 A1 | 12/2004 | Wenchell | |
| 2004/0260198 A1 | 12/2004 | Rothberg et al. | |
| 2004/0260337 A1 | 12/2004 | Freed | |
| 2005/0020884 A1 | 1/2005 | Hart et al. | |
| 2005/0033312 A1 | 2/2005 | Suzuki | |
| 2005/0033342 A1 | 2/2005 | Hart et al. | |
| 2005/0033357 A1 | 2/2005 | Braun | |
| 2005/0049580 A1 | 3/2005 | Brock et al. | |
| 2005/0085842 A1 | 4/2005 | Eversull et al. | |
| 2005/0090809 A1 | 4/2005 | Cooper et al. | |
| 2005/0107809 A1 | 5/2005 | Litscher et al. | |
| 2005/0124912 A1 | 6/2005 | Griego et al. | |
| 2005/0137609 A1 | 6/2005 | Guiraudon | |
| 2005/0148823 A1 | 7/2005 | Vaugh et al. | |
| 2005/0155611 A1 | 7/2005 | Vaugh et al. | |
| 2005/0192483 A1 | 9/2005 | Bonadio et al. | |

(56) References Cited

U.S. PATENT DOCUMENTS

| | | |
|---|---|---|
| 2005/0209608 A1 | 9/2005 | O'Heeron |
| 2005/0222582 A1 | 10/2005 | Wenchell |
| 2005/0228224 A1 | 10/2005 | Okada et al. |
| 2005/0267419 A1 | 12/2005 | Smith |
| 2005/0273084 A1 | 12/2005 | Hinman et al. |
| 2005/0273132 A1 | 12/2005 | Shluzas et al. |
| 2005/0277946 A1 | 12/2005 | Greenhalgh |
| 2006/0016853 A1 | 1/2006 | Racenet |
| 2006/0020241 A1 | 1/2006 | Piskun et al. |
| 2006/0020281 A1 | 1/2006 | Smith |
| 2006/0020287 A1 | 1/2006 | Lee et al. |
| 2006/0042636 A1 | 3/2006 | Nalagatla et al. |
| 2006/0071432 A1 | 4/2006 | Staudner |
| 2006/0094933 A1 | 5/2006 | Goldfarb et al. |
| 2006/0149137 A1 | 7/2006 | Pingleton et al. |
| 2006/0206145 A1* | 9/2006 | Griego et al. ............ 606/205 |
| 2006/0212062 A1 | 9/2006 | Farascioni |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0229641 A1 | 10/2006 | Gupta et al. |
| 2006/0229665 A1 | 10/2006 | Wales et al. |
| 2006/0241651 A1 | 10/2006 | Wilk |
| 2006/0241671 A1 | 10/2006 | Greenhalgh |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0258899 A1 | 11/2006 | Gill et al. |
| 2006/0259071 A1 | 11/2006 | Nicholas et al. |
| 2006/0259073 A1 | 11/2006 | Miyamoto et al. |
| 2006/0264706 A1 | 11/2006 | Piskun |
| 2006/0270911 A1 | 11/2006 | Voegele et al. |
| 2007/0027468 A1 | 2/2007 | Wales et al. |
| 2007/0049966 A1 | 3/2007 | Bonadio et al. |
| 2007/0060939 A1 | 3/2007 | Lancial et al. |
| 2007/0085232 A1 | 4/2007 | Brustad et al. |
| 2007/0088202 A1 | 4/2007 | Albrecht et al. |
| 2007/0088277 A1 | 4/2007 | McGinley et al. |
| 2007/0106317 A1 | 5/2007 | Shelton et al. |
| 2007/0118021 A1 | 5/2007 | Pokorney |
| 2007/0151566 A1 | 7/2007 | Kahle et al. |
| 2007/0156119 A1 | 7/2007 | Wallace et al. |
| 2007/0162072 A1 | 7/2007 | Nicholas et al. |
| 2007/0179525 A1 | 8/2007 | Frecker et al. |
| 2007/0185453 A1 | 8/2007 | Michael et al. |
| 2007/0208312 A1 | 9/2007 | Norton et al. |
| 2007/0244358 A1 | 10/2007 | Lee |
| 2007/0250113 A1 | 10/2007 | Hegeman et al. |
| 2007/0255219 A1 | 11/2007 | Vaugh et al. |
| 2007/0260114 A1 | 11/2007 | Miyamoto et al. |
| 2008/0027476 A1 | 1/2008 | Piskun |
| 2008/0039892 A1 | 2/2008 | Mitsuishi et al. |
| 2008/0051739 A1 | 2/2008 | McFarlane |
| 2008/0064921 A1 | 3/2008 | Larkin et al. |
| 2008/0065021 A1 | 3/2008 | Jenkins et al. |
| 2008/0065107 A1 | 3/2008 | Larkin et al. |
| 2008/0105730 A1 | 5/2008 | Racenet et al. |
| 2008/0119821 A1 | 5/2008 | Agnihotri et al. |
| 2008/0147113 A1 | 6/2008 | Nobis et al. |
| 2008/0154299 A1 | 6/2008 | Livneh |
| 2008/0177134 A1 | 7/2008 | Miyamoto et al. |
| 2008/0183044 A1 | 7/2008 | Colleran et al. |
| 2008/0188891 A1 | 8/2008 | Frank et al. |
| 2008/0255420 A1 | 10/2008 | Lee et al. |
| 2008/0255519 A1 | 10/2008 | Piskun et al. |
| 2008/0255608 A1 | 10/2008 | Hinman et al. |
| 2008/0262492 A1 | 10/2008 | Lee |
| 2008/0269727 A1 | 10/2008 | Lee |
| 2008/0294154 A1 | 11/2008 | Ibrahim et al. |
| 2008/0294191 A1 | 11/2008 | Lee |
| 2009/0005799 A1 | 1/2009 | Franer et al. |
| 2009/0062618 A1 | 3/2009 | Drew et al. |
| 2009/0084826 A1 | 4/2009 | Shah et al. |
| 2009/0088792 A1 | 4/2009 | Hoell, Jr. et al. |
| 2009/0112230 A1 | 4/2009 | Jinno |
| 2009/0171147 A1 | 7/2009 | Lee et al. |
| 2009/0206129 A1 | 8/2009 | Doll et al. |
| 2009/0306658 A1 | 12/2009 | Nobis et al. |
| 2009/0326325 A1 | 12/2009 | Naito et al. |
| 2010/0057121 A1 | 3/2010 | Piskun et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094289 A1 | 4/2010 | Taylor et al. |
| 2010/0130817 A1 | 5/2010 | Conlon |
| 2010/0179540 A1 | 7/2010 | Marczyk et al. |
| 2010/0228090 A1 | 9/2010 | Weisenburgh, II et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0228096 A1 | 9/2010 | Weisenburgh, II et al. |
| 2010/0228198 A1 | 9/2010 | Widenhouse et al. |
| 2010/0312060 A1 | 12/2010 | Widenhouse et al. |
| 2010/0312061 A1 | 12/2010 | Hess et al. |
| 2010/0312064 A1 | 12/2010 | Weisenburgh, II et al. |
| 2010/0312065 A1 | 12/2010 | Shelton, IV et al. |
| 2010/0331857 A1 | 12/2010 | Doyle et al. |
| 2011/0027269 A1 | 2/2011 | Marrotta et al. |
| 2011/0087269 A1 | 4/2011 | Stokes et al. |
| 2011/0230875 A1 | 9/2011 | Walberg et al. |
| 2012/0024099 A1 | 2/2012 | Main |
| 2012/0078243 A1 | 3/2012 | Worrell et al. |
| 2014/0039518 A1 | 2/2014 | Conlon et al. |
| 2015/0119918 A1 | 4/2015 | Blase et al. |

FOREIGN PATENT DOCUMENTS

| | | |
|---|---|---|
| DE | 94 19 138 U1 | 1/1995 |
| DE | 195 20 717 A1 | 12/1996 |
| DE | 20 2007 003093 U1 | 7/2007 |
| EP | 568383 A1 | 11/1993 |
| EP | 0621009 | 4/1994 |
| EP | 646358 A1 | 4/1995 |
| EP | 0776231 B1 | 6/1997 |
| EP | 950376 | 10/1999 |
| EP | 0966924 A1 | 12/1999 |
| EP | 0996925 A1 | 5/2000 |
| EP | 1219251 A1 | 7/2002 |
| EP | 1219252 A1 | 7/2002 |
| EP | 1219253 A1 | 7/2002 |
| EP | 1350476 | 10/2003 |
| EP | 1 621 139 A2 | 2/2006 |
| EP | 1731105 A1 | 12/2006 |
| FR | 2710270 A1 | 3/1995 |
| JP | 2000033089 A | 2/2000 |
| JP | 2006320750 | 11/2006 |
| WO | 94/26175 A1 | 11/1994 |
| WO | WO-9608208 A1 | 3/1996 |
| WO | WO-9608897 A1 | 3/1996 |
| WO | WO-9712557 A1 | 4/1997 |
| WO | WO-9729709 A1 | 8/1997 |
| WO | WO-9735521 A1 | 10/1997 |
| WO | WO-9810712 A1 | 3/1998 |
| WO | WO-9903536 A1 | 1/1999 |
| WO | WO-0030592 A1 | 6/2000 |
| WO | WO-0032253 A1 | 6/2000 |
| WO | WO-0217810 A2 | 3/2002 |
| WO | WO-0239890 A2 | 5/2002 |
| WO | WO-0239918 A1 | 5/2002 |
| WO | WO-02005854 A2 | 8/2002 |
| WO | WO-02094133 A1 | 11/2002 |
| WO | WO-03005890 A2 | 1/2003 |
| WO | WO-03067341 A2 | 8/2003 |
| WO | WO-03077730 A2 | 9/2003 |
| WO | WO-03091839 A2 | 11/2003 |
| WO | WO-2005087112 A1 | 9/2005 |
| WO | WO-2005094432 A2 | 10/2005 |

(56) References Cited

FOREIGN PATENT DOCUMENTS

| WO | WO-2006110733 A2 | 10/2006 |
|---|---|---|
| WO | WO-2007119232 A2 | 10/2007 |
| WO | WO-2008012787 A2 | 1/2008 |
| WO | WO-2008024502 A2 | 2/2008 |
| WO | WO-2009073577 A2 | 6/2009 |
| WO | 2010/030114 A2 | 3/2010 |

OTHER PUBLICATIONS

U.S. Appl. No. 12/399,482, filed Mar. 6, 2009 entitled Methods and Devices for Providing Access Into a Body Cavity.
U.S. Appl. No. 12/399,547, filed Mar. 6, 2009 entitled Surgical Access Devices and Methods Providing Seal Movement in Pre-defined Paths.
U.S. Appl. No. 12/399,625, filed Mar. 6, 2009 entitled Methods and Devices for Providing Access Into a Body Cavity.
U.S. Appl. No. 12/399,633, filed Mar. 6, 2009 entitled Methods and Devices for Providing Access Into a Body Cavity.
U.S. Appl. No. 12/399,656, filed Mar. 6, 2009 entitled Surgical Access Devices and Methods Providing Seal Movement in Pre-defined Movement Regions.
U.S. Appl. No. 12/512,542, filed Jul. 30, 2009 entitled Methods and Devices for Providing Access Into a Body Cavity.
U.S. Appl. No. 12/512,568, filed Jul. 30, 2009 entitled Methods and Devices for Providing Access Into a Body Cavity.
U.S. Appl. No. 12/766,086, filed Apr. 23, 2010 entitled Methods and Devices for Accessing a Body Cavity.
U.S. Appl. No. 12/775,699, filed May 7, 2010 entitled "Bendable Shaft for Handle Positioning".
"Applied GelPort Advanced Access Device," by Applied Medical Resources Corporation (Nov. 2002).
"Applied GelPort System" by Applied Medical Resources Corporation (2004).
"Bard® Bi-Directional and Kelly-Wick Tunnelers—Instructions for Use," by Bard Peripheral Vascular (Apr. 2006).
"intrack XT—Low Profile Atraumatic Clamps," by Novare Surgical Systems, Inc. (2002).
"1 Lap Disc Hand Access Device—Ref. Ld111," by Ethicon Endo-Surgery, Inc. (date unknown but no later than May 15, 2007, date of citation in U.S. Appl. No. 11/398,985; 1 page).
"Adult Cardiac Surgical Instruments," from the website of Genesee BioMedical, Inc. (date of first publication unknown; downloaded May 3, 2007; 4 pages).
"Hand Instruments," from the website of Olympus Surgical America (date of first publication unknown; downloaded May 3, 2007; 4 pages).
"Pen Competitors," (date of first publication unknown but no later than May 15, 2007, date of citation in U.S. Appl. No. 11/398,985; 1 page).
Advanced Surgical Concepts (ASC), 510(k) TriPort Laparoscopic Access Device, Dec. 26, 2007, 8 pages.
Ashida, R. et al., "Indocyanine Green is an Ideal Dye for Endoscopic Ultrasound-Guided Fine-Needle Tattooing of Pancreatic Tumors" *Endoscopy* 38, pp. 190-192 (2006).
Desai, M. et al., "Laprascopic and Robtoic Urology: Scarless single port transumbilical nephrectomy and pyeloplasty: first clinical report," Journal Compilation, 2008 BJU International, 101, 83-88.
http://www.innomedic.de/en/products/innomotion_overview.php (Innomedic Products), accessed Oct. 24, 2006.
http://www.intuitivesurgical.com/products/index.aspx (Intuitive Surgical Products), accessed Oct. 24, 2006.
http://www.lap-laser com/e/laser_m/prod/med.html (LAP Laser Application), accessed Oct. 24, 2006.
Ideas For Surgery.com, "Surgeon performs single-port laparoscopic surgery," dated Dec. 1, 2007.
Lee, D.I. et al., "Novel Approach to Minimizing Trocar Sites during Challenging Hand-Assisted Laparoscopic Surgery Utilizing the Gelport: Trans-Gel Instrument Insertion and Utilization," *Journal of Endourology*, vol. 17, No. 2, pp. 69-71 (Mar. 2003).
Maurin, et al., "A new robotic system for CT-guided percutaneous procedures with haptic feedback," LSIIT (UMR CNRS-ULP 7005), Louis Pasteur University, Bd. S. Brant, BP 10413, Strasbourg Illkirch 67412, France.
Maurin, et al., "A Parallel 5 DOF Positioner for Semi-Spherical Workspaces", Proceedings of DETC'04, ASME 2004 Design Engineering Technical Conferences and Computers and Information in Engineering Conference, Sep. 28-Oct. 2, 2004, Salt Lake City Utah USA.
Maurin, et al., "A Parallel Robotic System with Force Sensors for Percutaneous Procedures Under CT-Guidance", LSIIT (UMR CNRS-ULP 7005), Strasbourg I University Bd. S. Brant, BP 10413, 67412 Illkirch cedex, France.
Stoianovici, et al., "A Novel Mechanical Transmission Applied to Percutaneous Renal Access", DSC-vol. 61, Proceedings of the ASME Dynamic Systems and Control Division 1997.
Twentieth Edition—Illustrations of Surgical Instruments, by The Kny-Scheerer Company, New York, USA, pp. 1003, 1026, 1028-1029, 1133, 2034, 2068-2069, 2097-2099, 2132, 2137, 2144, 2155-2156, 2162, 2167-2171, 2173, 2175, 2244, 2255, 2281-2282, 2327, 2333, 2338- 2348, 2352, 2355, 2359, 2371, 3017, 3039-3073, 3132, 3165, 3168-3169, 3208-3209, 3219 (Jul. 1915).
URobitics, Brady Urological Institute, Johns Hopkins Medical Institutions, "Z-Stage PAKY", date of publication unknown but no later than Oct. 26, 2006 (date of citation in U.S. Appl. No. 11/307,231).
URobotics, Brady Urological Institute, Johns Hopkins Medical Institutions, "PAKY Needle Driver," date of publication unknown but no later than Oct. 26, 2006 (date of citation in U.S. Appl. No. 11/307,231).
URobotics, Brady Urological Institute, Johns Hopkins Medical Institutions, "The RCM Robot", date of publication unknown but no later than Oct. 26, 2006 (date of citation in U.S. Appl. No. 11/307,231).
Webpage of Novare Surgical, Inc. featuring clamps (date of first publication unknown; downloaded Feb. 23, 2004; 1 page).
International Preliminary Report on Patentability for Application No. PCT/US2011/035525, issued Nov. 13, 2012. (7 pages).
International Preliminary Report on Patentability for Application No. PCT/US2011/035526, issued Nov. 13, 2012. (7 pages).
International Search Report and Written Opinion for Application No. PCT/US2011/035525, issued Aug. 19, 2011. (12 pages).
International Search Report and Written Opinion for Application No. PCT/US2011/035526, issued Aug. 19, 2011. (12 pages).
International Search Report for PCT/US2011/035511 dated Oct. 10, 2011 (7 pages).

* cited by examiner

LAPAROSCOPIC DEVICES WITH FLEXIBLE ACTUATION MECHANISMS

FIELD OF THE INVENTION

The present invention relates to methods and devices for performing minimally invasive surgical procedures.

BACKGROUND OF THE INVENTION

Many surgical procedures involve inserting various instruments through the working channel of a surgical access device. The instruments are used to view, engage, and/or treat tissue within a body cavity or other surgical site to achieve a diagnostic or therapeutic effect. In laparoscopic abdominal procedures for example, the abdominal cavity is generally insufflated with $CO_2$ gas to a pressure of around 15 mm Hg. The abdominal wall is pierced and a plurality of tubular cannulas, each defining a working channel, are inserted at various points into the abdominal cavity. A laparoscopic telescope connected to an operating room monitor can be used to visualize the operative field and can be placed through one of the cannulas. Other laparoscopic instruments such as graspers, dissectors, scissors, retractors, etc. can be placed through the other cannula(s) to facilitate various manipulations by the surgeon. In this type of procedure, because of the positioning of the cannulas, it can be relatively easy to bring the tips of two separate surgical instruments together in a working relationship within the abdominal cavity. For example, a first instrument could be passed through a cannula in the left side of the patient's abdomen and operated with the surgeon's left hand while a second instrument could be passed through another cannula in the right side of the patient's abdomen and operated with the surgeon's right hand. The surgeon can then easily bring the tips of the two instruments together at an internal point, e.g., in the center of the patient's abdomen. A laparoscope viewing instrument can also be passed through a third cannula, positioned for example in the center of the patient's abdomen, such that the tips of the two instruments can be easily visualized from above.

In other surgical procedures, however, visualization and triangulation is not as straightforward. For example, in Single Incision Laparoscopic Surgery (SILS) or Single Site Laparoscopic Surgery (SSLS), a single laparoscopic entry point is formed, e.g., through the navel. An access device having one or more working channels, and typically a plurality of working channels, is then installed in the entry point and all instruments required for performing the surgery are inserted through this same access device. In such procedures, the elongate shafts of the various instruments end up being generally parallel to one another while inserted through the access device. This can make it very difficult to bring the tips of two instruments together within the abdominal cavity, especially if the instruments do not have distal articulation capabilities. In addition, since the viewing scope is inserted generally along the same axis as the various other instruments, it can be difficult or impossible to see the tips of the instruments. These problems can unduly lengthen the duration of the surgery, potentially increasing the risk of patient complications. Also, in cases where it is impossible to achieve adequate positioning of the instruments' tips and/or visualization, a second or even third entry point must be formed, increasing trauma to the patient and creating additional scars.

Furthermore, when a surgical instrument inserted in any way into the body, it can be difficult to optimally position the instrument's tip relative to target tissue at the surgical site. Particularly when an instrument is inserted from above a surgical site, e.g., through the abdominal wall, there are limited angles of approach to target tissue at the surgical site, which can make effective and quick use of the instrument difficult. Attempting to position an instrument's distal tip at an optimal position relative to a target tissue can require the surgeon's hand to be awkwardly positioned to hold the instrument at a desired angle to optimally position the instrument's distal tip. It can also be difficult for a surgeon to operate the instrument's tip, e.g., grab tissue using graspers, cut tissue using scissors, etc., when the surgeon's hand is bent at an awkward angle.

Moreover, if an instrument has distal articulation abilities, it can be difficult to effectively operate the instrument's tip when the instrument is distally articulated. Providing an adequate force around a bend in the distal articulated area to operate the tip can be difficult, e.g., because of size limitations of the instrument and remote operation of the tip from the instrument's handle.

Accordingly, there is a need for methods and devices which allow laparoscopic procedures to be performed with an enhanced ability to position and visualize surgical instruments.

SUMMARY OF THE INVENTION

The present invention generally provides methods and devices for performing minimally invasive surgical procedures. In one embodiment, an articulating laparoscopic device is provided that includes a cannulated elongate shaft having proximal and distal ends defining a longitudinal axis extending therebetween, an end effector coupled to the distal end of the shaft, and an articulator element effective to angularly orient the end effector beyond 45 degrees relative to the longitudinal axis of the shaft. The articulator element includes first and second rigid links. The first rigid link extends through the shaft and is movable longitudinally along a first link axis parallel to the longitudinal axis of the shaft. The second rigid link has a proximal end pivotally coupled to a distal end of the first rigid link, and has a distal end pivotally coupled to a proximal end of the end effector. Pushing the first rigid link distally along the first link axis causes the end effector to move from a first position in which the end effector is longitudinally aligned with the longitudinal axis of the shaft to a second position in which the end effector is angularly oriented relative to the longitudinal axis of the shaft.

The end effector can have a variety of configurations. The end effector can include, for example, graspers having opposed jaws movable between a closed position and an open position. In one embodiment, the end effector can be configured to articulate beyond 90 degrees relative to the longitudinal axis of the shaft. The second rigid link can be configured to pivot beyond 90 degrees relative to the longitudinal axis of the shaft to articulate the end effector beyond 90 degrees relative to the longitudinal axis of the shaft. In another embodiment, the end effector can be configured to articulate beyond 45 degrees relative to the longitudinal axis of the shaft in both clockwise and counterclockwise directions from the first position.

The first and second links can have also have a variety of configurations. For example, the first rigid link can be configured to move proximally along the first link axis to cause articulation of the end effector. For another example, pulling the first rigid link proximally along the first link axis can cause the end effector to move from the second position to the first position.

The device can optionally include a coupler coupling the end effector to the shaft and/or a stop element configured to limit articulation of the end effector to about 90 degrees relative to the longitudinal axis of the shaft. The coupler can alternatively or in addition be configured to limit articulation of the end effector to about 90 degrees relative to the longitudinal axis of the shaft.

In another embodiment, an articulating laparoscopic device is provided that includes a cannulated rigid elongate shaft having proximal and distal ends defining a longitudinal axis extending therebetween, an end effector coupled to the distal end of the shaft, and a rigid articulator element extending through the shaft. The articulator element is configured to move relative to the shaft to articulate the end effector about a pivot point at an articulation angle beyond 90 degrees relative to the longitudinal axis of the shaft.

The articulator element can vary in any number of ways. In one embodiment, the articulator element can be configured to articulate the end effector from a first position in which the end effector is longitudinally aligned with the shaft such that the articulation angle is about zero degrees to a second position in which the articulation angle is at least about 120 degrees. In another embodiment, the articulator element can include first and second rigid links. The first rigid link can extend through the shaft and can be configured to move longitudinally relative to the longitudinal axis of the shaft. The second rigid link can be coupled to a distal end of the first rigid link and can be configured to pivot in response to longitudinal movement of the first rigid link relative to the longitudinal axis of the shaft to cause articulation of the end effector. The end effector can be longitudinally aligned with the shaft such that the articulation angle is about zero degrees. Pushing the first rigid link distally can increase the articulation angle, or, in another embodiment, pulling the first rigid link proximally can increase the articulation angle.

The end effector, e.g., at least one of graspers, a dissector, a retractor, a light, a biopsy probe, a snare loop, forceps, scissors, a needle knife, and a sphincterotome, can also vary in any number of ways. For example, the end effector can be configured to articulate at least 45 degrees relative to the longitudinal axis of the shaft in both clockwise and counterclockwise directions from a position in which the end effector is longitudinally aligned with the longitudinal axis of the shaft. The end effector can be configured to articulate beyond 90 degrees relative to the longitudinal axis of the shaft in one of the clockwise and counterclockwise directions and to articulate no greater than 90 degrees relative to the longitudinal axis of the shaft in the other of the clockwise and counterclockwise directions.

In another aspect, a laparoscopic device is provided that includes an elongate shaft having proximal and distal ends defining a longitudinal axis extending therebetween, an end effector coupled to the distal end of the shaft, and an actuator element coupled to the end effector. The shaft has an inner lumen extending therethrough between the proximal and distal ends. The actuator element extends between the proximal and distal ends of the shaft along the longitudinal axis through the inner lumen, and the actuator element is configured to move relative to the shaft to actuate the end effector. The actuator element has at least a distal portion formed of a composite material.

The actuator element can have a variety of configurations. Rotation of the actuator element can be effective to move the opposed movable jaws of the end effector between open and closed positions. In one embodiment, the distal portion of the actuator element can be flexible, and a proximal portion of the actuator element can be rigid. The distal portion can include a core formed of a first material and an outer sheath surrounding the core. The outer sheath can be formed of a second material, e.g., a plastic, having a greater flexibility than a flexibility of the first material, e.g., a metal. In another embodiment, the distal portion can have a stiffness configured to change during actuation of the end effector.

The end effector can also have a variety of configurations. For example, the end effector can be configured to articulate up to an angle of at least 90 degrees relative to the longitudinal axis of the shaft.

The laparoscopic device can include an articulator element coupled to the end effector and extending through the inner lumen of the shaft between the proximal and distal ends of the shaft. The articulator element can be configured to articulate the end effector to angularly orient the end effector relative to the longitudinal axis of the shaft. The articulator element can extend through the inner lumen on one side of the inner lumen, and the actuator element can extend through the inner lumen on an opposite side of the inner lumen.

In another embodiment, a laparoscopic device is provided that includes a cannulated elongate shaft having proximal and distal ends defining a longitudinal axis extending therebetween, an end effector coupled to the distal end of the shaft, and an actuator element coupled to the end effector and extending through the shaft. The actuator element is configured to move relative to the shaft to actuate the end effector, and the actuator element includes a feature configured to change a stiffness of the actuator element when the actuator element moves to actuate the end effector.

The actuator element can vary in any number of ways. For example, the actuator element can be formed of a composite material. For another example, the actuator element can include a rigid proximal portion and a flexible distal portion. The flexible distal portion can include the feature, which can include an outer sheath surrounding a central core. The core is formed of, e.g., a metal, and the outer sheath can be formed of, e.g., a plastic. The outer sheath can optionally include a plurality of ribs extending radially outward from the core. The ribs can be configured to compress together to increase the stiffness of the actuator element when the actuator element moves to actuate the end effector. For yet another example, the actuator element can include a rigid actuator member extending through the shaft, and a flexible actuator member formed of a composite material. The flexible actuator member can have a proximal end coupled to a distal end of the rigid actuator member, and have a distal end coupled to the end effector. The rigid actuator member can be configured to translate longitudinally through the shaft to move the flexible actuator member relative to the shaft and to change the stiffness of the flexible actuator member to actuate the end effector.

The laparoscopic device can include an articulator element extending through the shaft along the longitudinal axis. The articulator element can be configured to articulate the end effector at an angle relative to the longitudinal axis of the shaft. The articulator element can extend through the shaft along one side thereof, and the actuator element can extend through the shaft along an opposite side thereof.

In another aspect, a laparoscopic surgical method is provided that includes inserting a cannulated elongate shaft of a surgical device into a body of a patient to position an end effector at a distal end of the shaft within the body. The device includes an actuator element extending through the shaft, and the actuator element is formed of a composite material in at least a flexible distal portion thereof. The method also includes translating the actuator element relative to the shaft to change a shape of at least the flexible distal portion to actuate the end effector.

The method can vary in any number of ways. In one embodiment, changing the shape of at least the flexible distal portion can include compressing together ribs extending radially outward from a central core of the flexible distal portion.

In another embodiment, a laparoscopic surgical method is provided that includes inserting a rigid elongate shaft of a surgical device into a body of a patient to position an end effector at a distal end of the shaft within the body, and translating a rigid articulator element extending through an inner lumen of the shaft along an axis parallel to a longitudinal axis of the shaft to articulate the end effector about a pivot point beyond 90 degrees relative to the longitudinal axis of the shaft.

The method can have any number of variations. In one embodiment, translating a rigid articulator element can include pushing the articulator element distally along the axis parallel to the longitudinal axis of the shaft.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
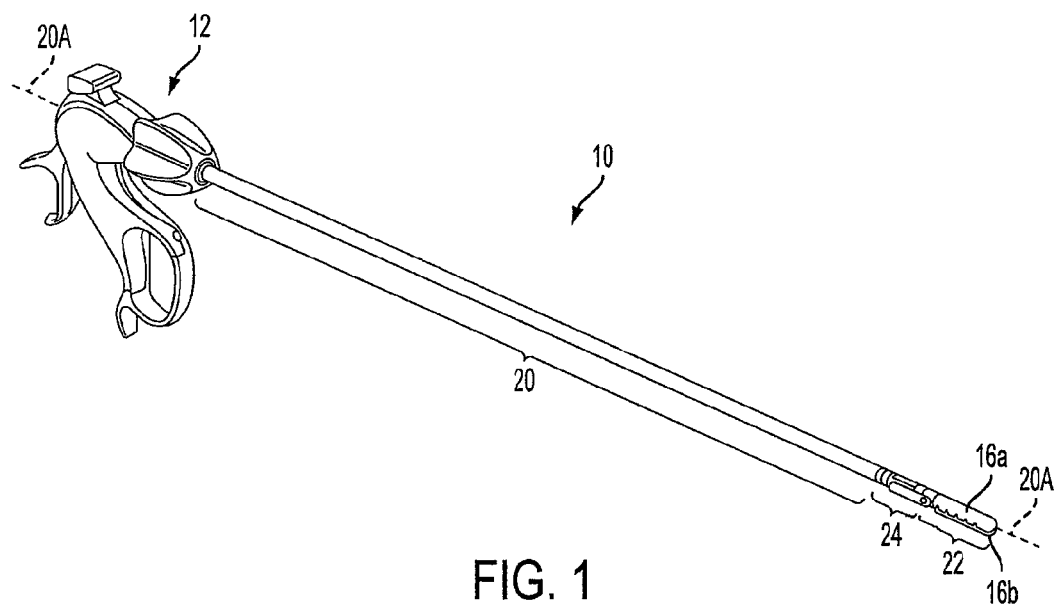
FIG. 1 is a perspective view of a laparoscopic device including a handle and a shaft extending distally from the handle, the shaft having an articulatable end effector coupled to a distal end thereof.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary devices and methods are provided for performing minimally invasive surgical procedures. In general, the devices and methods allow a working end of a surgical instrument to articulate at an angle beyond 45 degrees, thereby facilitating optimal positioning of the working end relative to a surgical site and to any nearby surgical instruments. In an exemplary embodiment, a laparoscopic device includes an elongate shaft having an end effector at a distal end thereof. The end effector can be configured to be movable between a first configuration in which the end effector is longitudinally aligned with or linear relative to the shaft and a second configuration in which the end effector is articulated at an angle beyond 45 degrees relative to the shaft. With the end effector in the first configuration or in the second configuration, the device can be configured to allow selective actuation of the end effector, e.g., opening and/or closing of jaws, application of energy such as for cutting or for cauterization, extension of a needle, collection of a biopsy sample, etc. In this way, the end effector can achieve a relatively high degree of articulation, e.g., beyond 45 degrees, while still being functionally effective. The device can thus be inserted into a patient's body with the end effector in the first configuration, and the device can be subsequently manipulated to move the end effector from the first configuration to the second configuration to allow the device's working distal end, e.g., the end effector, to be optimally angled within the body relative to a surgical site and/or to any other nearby surgical instruments. By being articulatable beyond 45 degrees, an instrument can be inserted substantially above a surgical site, e.g., inserted into the abdominal cavity through the navel, while being configured to approach the surgical site and/or other instruments at a variety of angles and while being selectively actuatable at any articulated position. Such an instrument configuration can also be particularly advantageous where two or more instruments are inserted into a patient's body cavity through the same entry port in tissue because it can allow the instruments' working ends to each angle beyond 45 degrees to be brought together without requiring awkward surgeon positioning. In particular, distal tips of the instruments can be brought together at a single point within the body cavity, even though the instruments' shafts extend generally parallel to one another.

A person skilled in the art will appreciate that while the methods and devices are described in connection with laparoscopic procedures in which one or more surgical instruments are inserted into a patient's body through an artificial opening, e.g., an incision, the methods and devices disclosed herein can be used in numerous surgical procedures and with numerous surgical instruments. By way of non-limiting example, the methods and devices can be used in open surgical procedures.

A person skilled in the art will also appreciate that the devices disclosed herein can be inserted into a body in any way, such as through a natural orifice, through an incision or puncture hole formed in tissue, etc. The devices can be inserted directly into a patient's body or can be inserted through an access device having a working channel through which a shaft of a surgical instrument can be advanced. A person skilled in the art will further appreciate that an access device can be configured to allow insertion of a single surgical instrument therethrough, such as with a straight cannula, or to allow simultaneous insertion of multiple instruments therethrough, such as with a surgical access device having multiple sealing ports each defining a working channel. Devices disclosed herein can alternatively or additionally be introduced into a body through an auxiliary passageway along the outside of a scoping device or other surgical instrument, as will be appreciated by a person skilled in the art. Exemplary embodiments of a surgical instrument that provides such an auxiliary passageway are described in more detail in U.S. Pat. No. 7,615,005 issued Nov. 10, 2009 entitled "Medical Apparatus For Use With An Endoscope," which is hereby incorporated by reference in its entirety.

In an exemplary embodiment, shown in FIG. 1, a surgical device 10 is provided that includes a proximal handle 12 having an elongated tubular shaft 20 extending distally therefrom. The shaft 20 can have a working element or end effector 22, generally referred to as an "end effector," at a distal end thereof. A rigid coupler 24 can optionally couple the end effector 22 to the shaft 20, with a proximal end of the coupler 24 being coupled to a distal end of the shaft 20 and a distal end of the coupler 24 being coupled to a proximal end of the end effector 22. The end effector 22 in the illustrated embodiment includes a tissue grasper having a pair of opposed jaws 16a, 16b configured to move between open and closed positions, but as will be appreciated by a person skilled in the art, the end effector 22 can include any tool, e.g., a grasper, a dissector, scissors, forceps, a retractor, a light, a biopsy probe, a snare loop, a needle knife, a sphincterotome, etc. As discussed further below, the handle 12 can be configured to operate the end effector 22 and/or to rotate the shaft 20.

Figure 2:
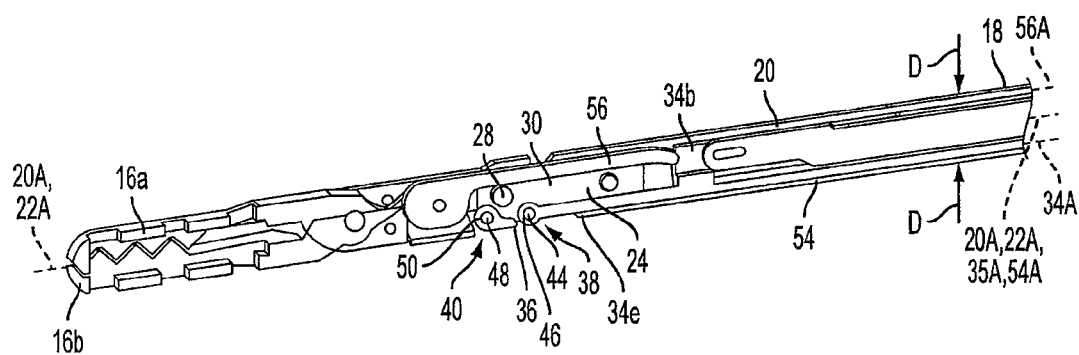
FIG. 2 is a cross-sectional perspective view of a distal portion of the device of FIG. 1.
Figure 3:
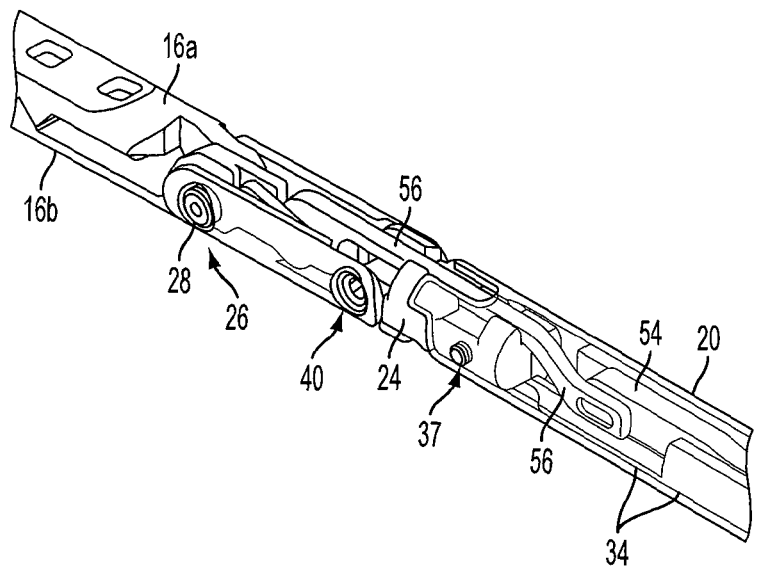
FIG. 3 is a perspective, partially transparent view of a distal portion of the device of FIG. 1.

The shaft 20 can have a variety of sizes, shapes, and configurations. The shaft 20 can be rigid, flexible, or a combination thereof, but in an exemplary embodiment it is rigid, e.g., made from a generally non-bendable material such as a hard polymer or titanium. Portions of the shaft 20 can be less flexible or more rigid than a remainder of the shaft 20 to facilitate insertion through tissue. As mentioned above, the shaft 20 can be tubular, and it can have an inner lumen 18 extending through at least a proximal portion thereof, as shown in FIGS. 2 and 3. As discussed further below, an articulator element and an actuator element can each be at least partially positioned within the inner lumen 18. Generally, the articulator element can be configured to move relative to the shaft 20 to angularly orient the end effector 22 relative to a longitudinal axis 20A of the shaft 20, and the actuator element can be configured to move relative to the shaft 20 to actuate the end effector 22, e.g., to open and close the jaws 16a, 16b.

Figure 4:
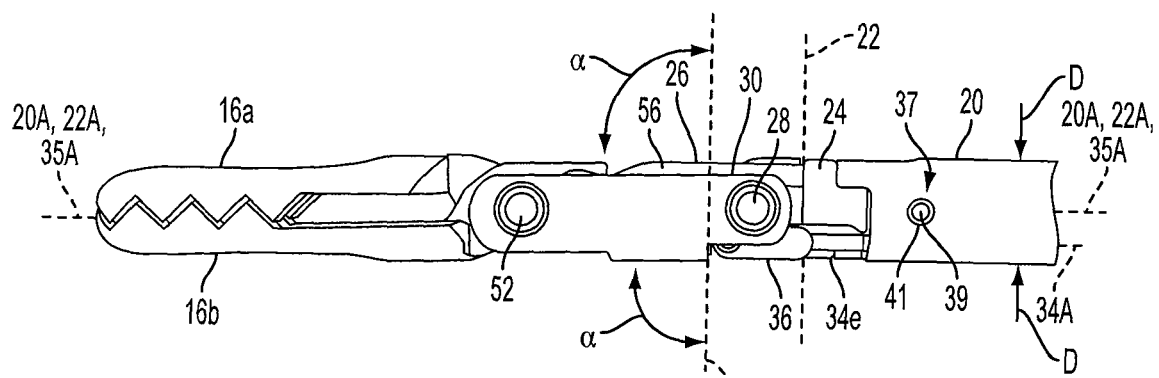
FIG. 4 is a side view of a distal portion of the device of FIG. 1.

The shaft 20 can have any longitudinal length, although in an exemplary embodiment it is long enough to allow the handle 12 to be manipulated outside a patient's body when the shaft 20 extends through an opening in the body with the end effector 22 disposed within a body cavity, e.g., have a longitudinal length of about 33 cm. In this way, the end effector 22 can be easily manipulated when the device 10 is in use during a surgical procedure. As illustrated in FIGS. 2 and 4, the shaft 20 can have any diameter D, e.g., less than or equal to about 10 mm, and more particularly less than or equal to about 5 mm, to allow for insertion of the shaft 20 through an access device, such as during a laparoscopic surgical procedure. The end effector 22 mated to the shaft's distal end, and in one embodiment can have a diameter equal to or less than the shaft's diameter D, at least when the jaws 16a, 16b are in a closed position, to further facilitate insertion of the device's distal portion into a patient's body.

Figure 5:
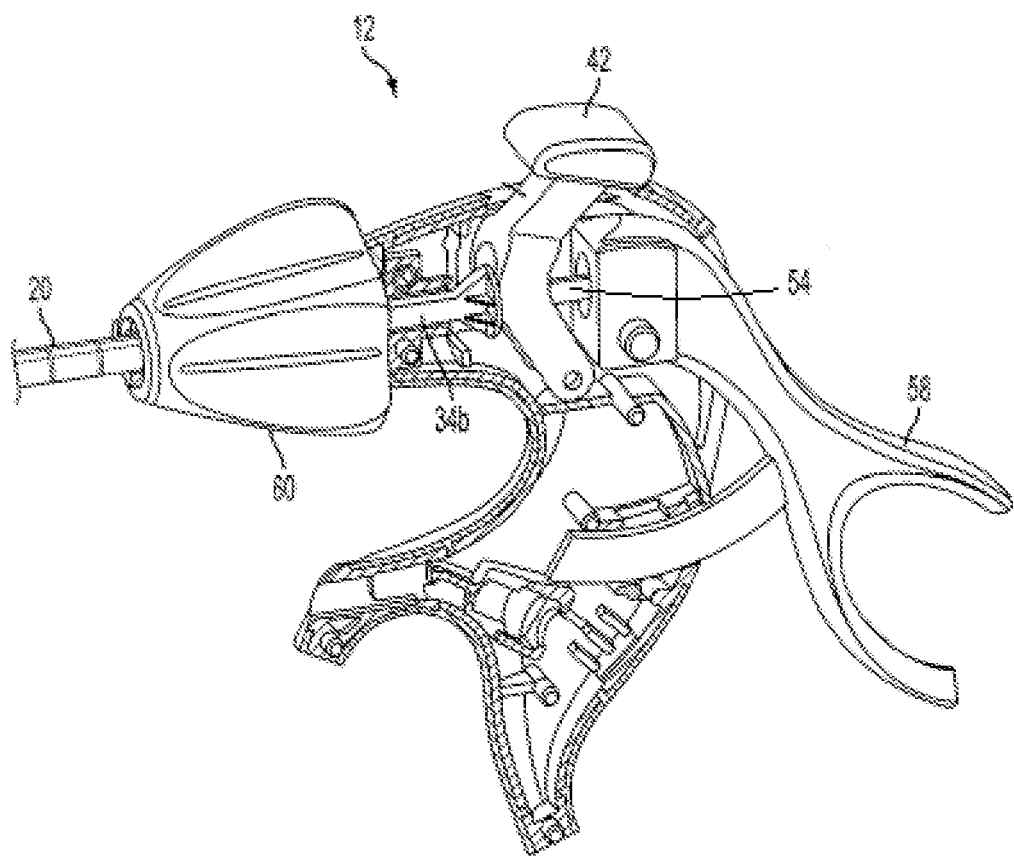
FIG. 5 is a perspective view of a proximal portion of the device of FIG. 1, with a housing removed from a handle of the device.
Figure 6:
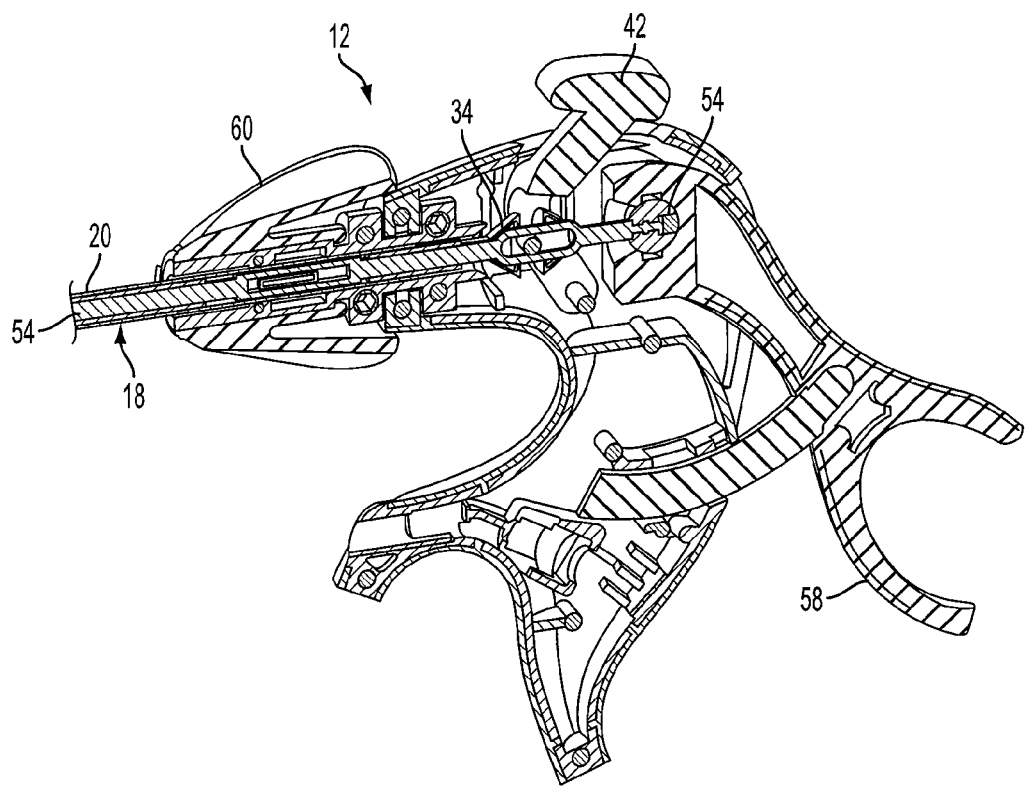
FIG. 6 is a cross-sectional perspective view of a proximal portion of the device of FIG. 1.

As shown in FIGS. 5 and 6, a proximal portion of the shaft 20 can be disposed within the handle 12 with a remainder of the shaft 20 extending distally from the handle 12. As shown in FIGS. 1, 5, and 6, the shaft 20 can extend distally from the handle 12 in a generally straight line along a longitudinal axis 20A. In other exemplary embodiments, the shaft 20 can have a bend or curvature near its proximal end. Such a bend or curvature can be helpful in preventing handles of two instruments from interfering with the other in a so-called "chopstick" effect when two or more instruments are inserted in closely-spaced instrument openings or closely spaced trocars. As will be appreciated by a person skilled in the art, a bend or curvature in the proximal portion of the shaft 20 can be fixed, or alternatively, it can be movable, such as in the form of a flexible "elbow" that can be adjusted, such as manually, at the point of use.

In an exemplary embodiment, the shaft 20 can be substantially cylindrical to help the shaft 20 pass smoothly into a body. The shaft 20 can have any constant or varying shape along its longitudinal length, and the shaft's diameter D can be uniform or non-uniform along its longitudinal length. In an exemplary embodiment, as shown in FIG. 1, the shaft 20 can have a substantially uniform diameter D along its longitudinal length.

Figure 7:
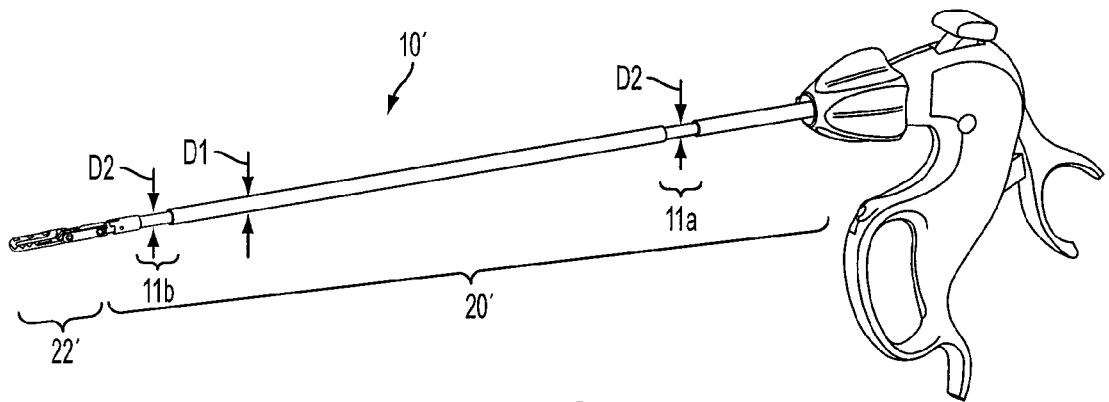
FIG. 7 is a perspective view of another embodiment of a laparoscopic device including a handle and a shaft extending distally from the handle, the shaft having an articulatable end effector coupled to a distal end thereof.

In another embodiment, as shown in FIG. 7, a surgical device 10' can generally be configured and used similar to the device 10 of FIGS. 1-6, but an elongate tubular shaft 20' of the device 10' can have an end effector 22' at a distal end thereof and can have a first, substantially uniform diameter D1 along its longitudinal length except at one or more locations therealong, e.g., at first and second reduced diameter portions 11a, 11b, having a second diameter D2 less than the first diameter D1. Although the shaft 20' has two reduced diameter portions, a person skilled in the art will appreciate that the shaft 20' can have any number of reduced diameter portions. The reduced diameter portions 11a, 11b can facilitate surgery in any number of ways, e.g., help reduce surgical clutter and/or help facilitate visual confirmation of the device's position. The first and second reduced diameter portions 11a, 11b can, as in the illustrated embodiment, be respectively located in proximal and distal portions of the shaft 20', which can help facilitate visual confirmation of the device's position relative to a patient and/or other surgical instruments by the relative positioning of the first and second reduced diameter portions 11a, 11b to the patient and/or the other surgical instruments. As will be appreciated by a person skilled in the art, the first and second reduced diameter portions 11a, 11b can have same or different diameters from one another, and can be integrally formed with a reminder of the shaft 20' or can be discrete elements coupled thereto.

Figure 8:
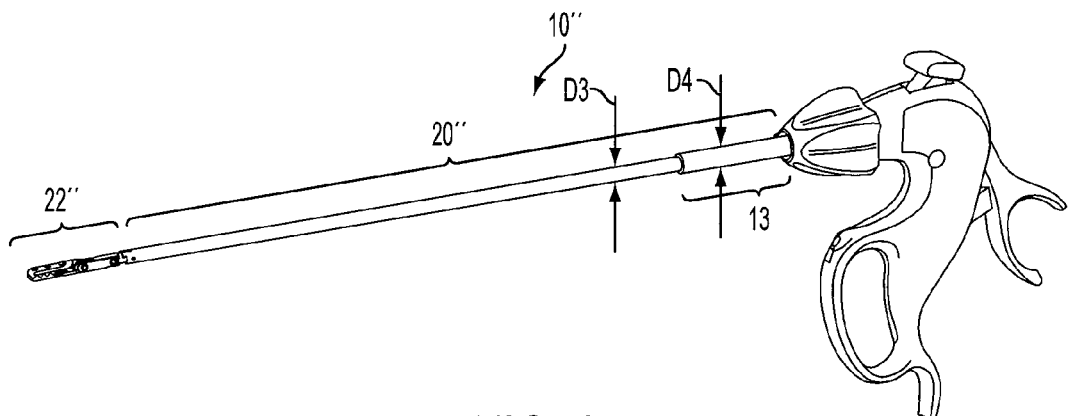
FIG. 8 is a perspective view of yet another embodiment of a laparoscopic device including a handle and a shaft extending distally from the handle, the shaft having an articulatable end effector coupled to a distal end thereof.
Figure 9:
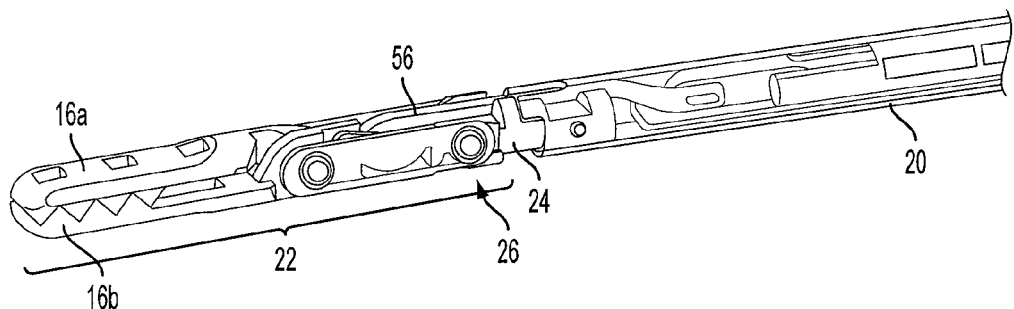
FIG. 9 is another perspective, partially transparent view of a distal portion of the device of FIG. 1.
Figure 10:
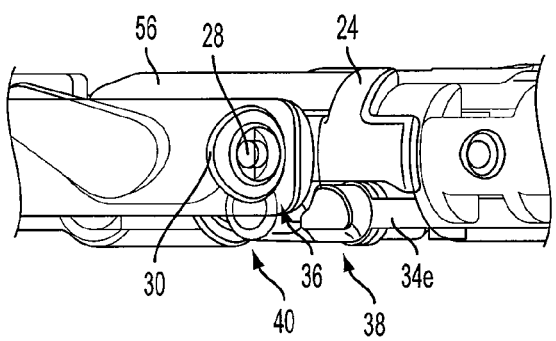
FIG. 10 is a perspective, partially transparent view of a distal portion of the device of FIG. 1.

In another embodiment, as shown in FIG. 8, a surgical device 10" can generally be configured and used similar to the device 10 of FIGS. 1-6, but an elongate tubular shaft 20" of the device 10" can have an end effector 22" at a distal end thereof and can have a first, substantially uniform diameter D3 along its longitudinal length except at one or more locations therealong, e.g., at an enlarged diameter portion 13, having a second diameter D4 greater than the first diameter D3. Although the shaft 20" has one reduced diameter portion, a person skilled in the art will appreciate that the shaft 20" can have any number of enlarged diameter portions. The enlarged diameter portion 13 can facilitate surgery in any number of ways, e.g., help facilitate manipulation of the device 10". The enlarged diameter portion 13 can, as in the illustrated embodiment, be located in a proximal portion of the shaft 20" and be configured as a stop member to help prevent the shaft 20" from being distally passed through an incision or an access device beyond a certain point, e.g., until a distal end of the enlarged diameter portion 13 abuts skin or an access device to stop the shaft 20" from further distal insertion into a patient's body. The devices 10', 10" of FIGS. 7 and 8 are discussed in more detail in U.S. patent application Ser. No. 12/775,699 entitled "Bendable Shaft For Handle Positioning" filed on May 7, 2010, which is hereby incorporated by reference in its entirety.

Referring again to FIGS. 1-6, as mentioned above, the end effector 22 can be configured to articulate relative to the shaft 20 to angularly orient the end effector 22. The proximal end of the end effector 22 can be pivotally coupled to the distal end of the coupler 24 at a first pivot point 26, about which the end effector 22 can pivot or articulate, e.g., move in a single plane, relative to the coupler 24 and to the shaft 20. The end effector 22 and the coupler 24 can be pivotally connected together at the first pivot point 26 in a variety of ways to movably couple together, as will be appreciated by a person skilled in the art. As in the illustrated embodiment shown in FIGS. 2-6 and 9-13, a pin 28 can be inserted, e.g., by press fit, through a pivot hole 30 formed in the proximal end of the end effector 22 and a pivot hole formed in the distal end of the coupler 24 to form a pivot hinge-type joint at the first pivot point 26 between the end effector 22 and the coupler 24. A proximal end of the coupler 24 can be coupled to a distal end of the shaft 20 in any way. As in the illustrated embodiment, shown in FIGS. 3 and 4, the coupler 24 and the shaft 20 can be non-pivotally coupled together at a non-pivoting point 37 with pins 39 extending radially outward from opposite sides of the coupler 24 being fixed in corresponding holes 41 formed in opposite sides of the shaft 20. The end effector 22 can be coupled to a distal end of the shaft 20 without the intervening coupler 24, as will be appreciated by a person skilled in the art.

Figure 11:
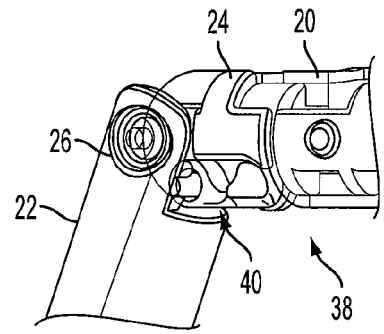
FIG. 11 is a perspective, partially transparent view of a distal portion of the device of FIG. 1 showing the end effector in an articulated configuration.
Figure 12:
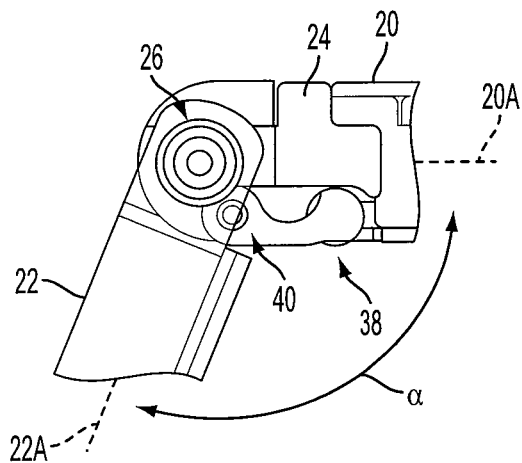
FIG. 12 is a side, partially transparent view of the distal portion of the device of FIG. 11.
Figure 13:
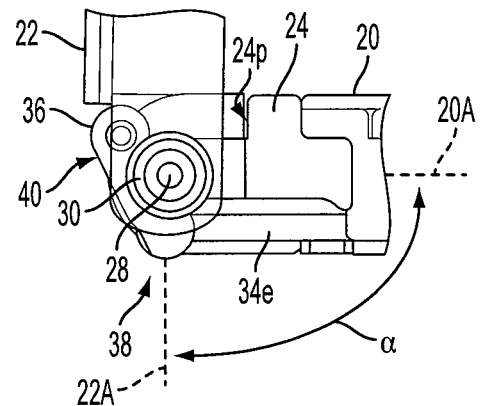
FIG. 13 is a side, partially transparent view of a distal portion of the device of FIG. 1 showing the end effector in an articulated configuration.

As mentioned above, the device 10 can include an articulator element configured to articulate the end effector 22 to angularly orient the end effector 22 relative to the longitudinal axis 20A of the shaft 20. The articulator element can have a variety of configurations, but in the illustrated embodiment the articulator element includes a rigid element extending at least partially through the shaft 20 and the coupler 24 and being configured to move relative thereto to pivot or articulate the end effector 22 about the first pivot point 26. Having a rigid articulator element can help maximize stability and rigidity of the end effector's angulation and allow the end effector 22 to be more securely moved to and maintained at any angle throughout its range of motion. Generally, moving the articulator element relative to the shaft 20 can cause the end effector 22 to move between the first configuration in which a longitudinal axis 22A of the end effector 22 is aligned with or parallel to the shaft's longitudinal axis 20A, as shown in FIGS. 2-4, 9, and 10, and the second configuration in which the end effector 22 is articulated relative to the shaft's longitudinal axis 20A with the end effector's longitudinal axis 22A angled at a non-zero angle from the shaft's longitudinal axis 20A, as shown in FIGS. 11-13 and as shown in FIG. 4 with the end effector 22 in phantom lines.

As shown in FIGS. 2-6 and 9-13, the articulator element can include a rigid multi-bar system including a proximal rigid articulator bar, link, or rod 34, generally referred to as a "proximal link," extending through the shaft 20 and a distal rigid articulator bar, link, or rod 36, generally referred to as a "distal link." The proximal and distal links 34, 36 can each have a variety of sizes, shapes, and configurations. The proximal and distal links 34, 36 can be solid or can have one or more hollow portions, same or different from one another. As in the illustrated embodiment, the distal link 36 can include a solid member having a longitudinal length that is less than a longitudinal length of the proximal link 34, which as discussed further below can have a longitudinal length that allows it to extend from the handle 12, through the shaft 20, and distally beyond the distal end of the shaft 20 at least when the end effector 22 is articulated. The distal link 36 can have a longitudinal length that is less than the diameter D of the shaft 20, e.g., less than an inner diameter of the shaft's inner lumen 18. In this way, throughout the distal link's range of motion, e.g., with the distal link 36 pivoted at the second pivot point 38 to articulate the end effector 22 at any angle α relative to the shaft's axis 20A, the distal link 36 can be configured to not extend beyond the shaft's diameter D, thereby helping to prevent the device 10 from snagging on and/or damaging adjacent tissue when the end effector 22 is articulated. As discussed further below, the distal link's longitudinal length can at least partially define a maximum degree of articulation of the end effector 22.

The distal link 36 can have a proximal end pivotally coupled to a distal end of the proximal link 34 at a second pivot point 38, and a distal end of the distal link 36 can be pivotally coupled to a proximal end of the end effector 22 at a third pivot point 40. A proximal end of the proximal link 34 can be operatively coupled to a lever 42 at the handle 12, illustrated in FIGS. 6 and 7 and discussed further below. Although in the illustrated embodiment the proximal link 34 extends from the handle 12 to the distal link 36, in some embodiments, an additional rigid rod can couple to the proximal link's proximal end and extend from the proximal link's proximal end to the handle 12. Furthermore, as will be appreciated by a person skilled in the art, the additional rigid rod can include multiple rigid rods.

As in the illustrated embodiment, the proximal link 34 can be an elongate tubular body 34b at least partially slidably disposed in the inner lumen 18 of the shaft 20. The interior of the proximal link 34 can be cannulated to allow the actuator element to be movably disposed therein, as discussed further below. A protrusion or extension 34e, e.g., a rod, bar, or link, generally referred to as an "extension rod," can extend distally from a perimeter or circumference of the elongate tubular body 34b at a distal end thereof, and the extension rod 34e can be coupled at its distal end to the distal link's proximal end at the second pivot point 38. The extension rod 34e can have a diameter less than a diameter of the elongate tubular body 34b, which can allow the extension rod's longitudinal axis 34A to be laterally or radially offset from the elongate tubular body's central longitudinal axis as well as laterally or radially offset from the shaft's central longitudinal axis. In the illustrated embodiment, the shaft's central longitudinal axis is the same as the shaft's longitudinal axis 20A, and the elongate tubular body's central longitudinal axis is the same as the elongate tubular body's longitudinal axis 35A. In other words, at least a distal portion of the articulator element can have a reduced diameter region, thereby allowing a distal portion of the actuator element to be disposed parallel thereto and on an opposite side of the shaft's lumen 18, as discussed further below. A person skilled in the art will appreciate that while the articulator element extends at least partially through the shaft's inner lumen 18 in the illustrated embodiment, at least a portion of the articulator element can be disposed outside the shaft 20, e.g., be slidably movable within a channel formed in an exterior surface of the shaft 20. Similarly, a person skilled in the art will also appreciate that while the articulator element extends at least partially through a channel formed in an exterior surface of the coupler 24 in the illustrated embodiment, at least a portion of the articulator element can be disposed inside the coupler 24, e.g., be slidably movable within an inner lumen of the coupler 24.

The end effector 22 and the proximal and distal links 34, 36 can be pivotally coupled together in any way at their associated ones of the second and third pivot points 38, 40, as will be appreciated by a person skilled in the art. As in the illustrated embodiment shown in FIG. 2 a second pin 44 can be inserted, e.g., by press fit, through respective second holes 46 formed in the distal end of the proximal link 34 and the proximal end of the distal link 36 to form a pivot hinge-type joint at the second pivot point 38 between the adjacent proximal and distal links 34, 36. Similarly, a third pin 48 can be inserted through respective third holes 50 formed in the distal end of the distal link 36 and the proximal end of the end effector to form a pivot hinge-type joint at the third pivot point 40 between the adjacent distal link 36 and end effector 22.

When the end effector 22 is in the first configuration, e.g., the end effector's longitudinal axis 22A is co-axial or parallel to the shaft's longitudinal axis 20A, the articulator element can be in a corresponding straight configuration in which a longitudinal axis thereof is co-axial or parallel to the shaft's longitudinal axis 20A. In other words, when the end effector 22 is unarticulated, the longitudinal axes 35A, 34A of the proximal and distal links 34, 36, respectively, can be parallel to each other and co-axial or parallel to the shaft's longitudinal axis 20A, as shown in FIG. 2. With the end effector 22 in the second, articulated configuration, the axes 22A, 34A of the end effector 22 and the distal link 34 can intersect the longitudinal axes 20A, 35A of the shaft 20 and the proximal link 34.

In response to selective movement of the lever 42, the proximal link 34 can be configured to move longitudinally in both proximal and distal directions along its longitudinal axis 35A co-axial or parallel to the shaft's longitudinal axis 20A. A person skilled in the art will appreciate that as an alternative to the lever 42, other types of controls, e.g., a trigger, a knob, a button, a spring mechanism, etc., can be included with the handle 12 for applying a longitudinal force to the proximal link 34 co-axial or parallel to the shaft axis 20A to articulate and/or straighten the end effector 22. Longitudinal movement of the proximal link 34 can be configured to impart force or motion to the distal link 36, thereby causing the end effector 22 to pivot about the first and third pivot points 26, 40 to be angularly oriented relative to the shaft's axis 20A. Longitudinal movement of the proximal link 34 can cause the distal link 36 to move longitudinally along the distal link's axis 34A parallel to the shaft's axis 20A, e.g., if the proximal link 34 is pulled, or cause the distal link 36 to pivot about the second pivot point 38 such that the distal link 36 is angularly oriented relative to the shaft's axis 20A. In other words, movement of the proximal link 34 can be fixed along its longitudinal axis 35A, while the distal link 36 can be configured to pivot or rotate away from the shaft's axis 20A relative to the proximal link 34 and to the shaft 20. The presence of the coupler 24 can help provide sufficient space for the articulator element to move distally beyond the shaft 20 to articulate the end effector 22 without the articulator element extending distally beyond the end effector 22 or extending beyond the shaft's diameter D.

Generally, pushing the articulator element distally relative to the shaft 20 can cause the end effector 22 to move from the first configuration in which the longitudinal axis 22A of the end effector 22 is co-axial or parallel to the shaft's longitudinal axis 20A, as shown in FIGS. 2-4, 9, and 10, to the second configuration in which the end effector 22 is articulated relative to the shaft's longitudinal axis 20A with the end effector's longitudinal axis 22A angled at a non-zero angle from the shaft's longitudinal axis 20A, as shown in FIGS. 11-13 and with phantom dotted lines in FIG. 4. Similarly, when the end effector 22 is in the second configuration, pulling the articulator element proximally relative to the shaft 20 can move the end effector 22 from the second configuration to the first configuration. The end effector 22 is shown in FIG. 13 at a maximum articulated position of 90°, e.g., at an angle α of 90° relative to the shaft's axis 20A.

The end effector 22 can be configured to move from the first configuration to the second configuration by pivoting about the first pivot point 26 in clockwise and/or counterclockwise directions. As in the illustrated embodiment, as shown by the end effector 22 in phantom dotted lines in FIG. 4, the end effector 22 can be configured to pivot 90°, e.g., with the angle α between the end effector's axis 22A and the shaft's axis 20A equaling 90°, in both clockwise and counterclockwise directions about the first pivot point 26. The end effector 22 can be moved from the first configuration by pivoting in one of the clockwise and counterclockwise directions by pushing the articulator element, e.g., moving the articulator element proximally relative to the shaft 20, as shown in FIG. 13. As the proximal link 34 is pushed distally by a driving force in the handle 12, e.g., by moving the articulator lever 42 in a proximal direction, the proximal link 34 in turn pushes the distal link 36 distally relative to the shaft 20. As the links 34, 36 are pushed distally, the proximal link 34 applies a force on the distal link 36 to pivot the distal link 36 about the second pivot point 38 such that the distal end of the distal link 36 moves radially or laterally away from the extension rod's longitudinal axis 34A while the distal link's proximal end pivots about the second pivot point 38. The movement of the distal link's distal end applies a force on the end effector 22 to pivot the end effector 22 about the first pivot point 26 to angularly orient the end effector 22 relative to the shaft's axis 20A. The off-center locations of the second and third pivot points 38, 40, e.g., along the distal link's axis 34A radially offset from the shaft's central axis 20A, can result in the distal link 36 and the end effector 22 pivoting in a predetermined direction in response to the pushing force of the proximal link 34. Similarly, the end effector 22 can be moved from the first configuration by pivoting in the other one of the clockwise and counterclockwise directions by pulling the articulator element, e.g., moving the articulator element proximally relative to the shaft 20, as shown in FIGS. 11 and 12. FIGS. 11 and 12 also illustrate that when the articulator element is pulled to pivot the end effector 22 in the other one of the clockwise and counterclockwise directions, the distal link 36 moves along an axis parallel to the shaft's axis 20A and coaxial with or parallel to the extension rod's longitudinal axis 34A, e.g., the distal link's distal end does not move radially or laterally relative to the extension rod's longitudinal axis 34A. In this way, the end effector 22 can be optimally positioned in a variety of angular positions, e.g., by angling clockwise or counterclockwise, without requiring rotation or other movement of the shaft 20. FIGS. 11 and 12 also show the end effector 22 in the second configuration with the angle α being between the end effector's minimum 0° and maximum 90°.

The articulator element can also be moved proximally and/or distally relative to the shaft 20 to move the end effector 22 from one articulated configuration to another articulated configuration, e.g., between different non-zero angles α, including between +/−values of the same angle α. The device 10 can optionally include a lock mechanism configured to fixedly hold the end effector 22 in the second configuration, e.g., at a selected angular orientation. As will be appreciated by a person skill in the art, the lock mechanism can have a variety of configurations, such as a toothed rack and pawl, a depressible button configured to engage any one of a plurality of holes, etc. The degree of the angle α between the end effector's and shaft's axes 22A, 20A can be varied by varying the pulling/pushing force on the articulator element. Varying the size of the angle α can change the direction of approach of end effector 22 to an intended site, which can assist in allowing for more precise positioning of the end effector 22. A person skilled in the art will appreciate that the force imparted from the proximal link 34 to the distal link 36 and from the distal link 36 to the end effector 22 can be simultaneous despite the presence of minimal delays as forces translate along the articulator element.

As mentioned above, the longitudinal length of the distal link 36 can at least partially define the maximum value of the angle α, with longer longitudinal lengths of the distal link corresponding to smaller maximum values of the angle α. In the illustrated embodiment, the distal link's longitudinal length is substantially equal to the shaft's diameter D. The coupler 24 can also be configured to at least partially define the maximum value of the angle α. The coupler 24 can have a proximal surface 24p, as shown in the illustrated embodiment in FIG. 13, configured to engage and abut an exterior surface of the end effector 22 when the end effector 22 is articulated to a certain angle α, thereby preventing the angle α from increasing beyond a certain maximum value by preventing the end effector 22 from pivoting further about the first and third pivot points 26, 40. In this way, even if an attempt was made to push the articulator element distally when the end effector 22 abuts the coupler's proximal surface 24p, the articulator element would be prevented from so moving distally, or, indeed, at all. In the illustrated embodiment, the articulation angle α can be in a range from −90° to +90°.

Figure 14:
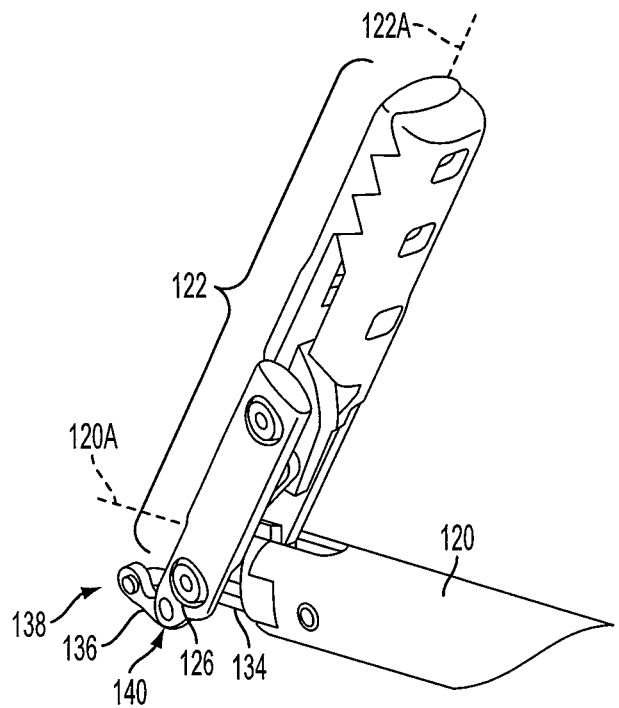
FIG. 14 is a perspective view of a distal portion of another embodiment of a laparoscopic device including a shaft having an articulatable end effector coupled to a distal end thereof, the end effector being shown in an articulated configuration.

In another embodiment, illustrated in FIG. 14, a surgical device can be similar to the device 10 of FIGS. 1-6 and 9-13, however can be configured to allow an end effector 122 at a distal end of the elongate tubular shaft 120 to articulate beyond 90° relative to the shaft's longitudinal axis 120A, e.g., to at least about 120°, such as up to about 130°. As shown in FIG. 14, the device can include a rigid articulator element including rigid proximal and distal links 134, 136, with a distal end of the proximal link 134 being coupled to a proximal end of the distal link 136 at a second pivot point 138. The distal link 136 of FIG. 14 also has a longitudinal length less than that of the distal link 36 in the device 10 of FIGS. 1-6 and 9-13, which can define a degree of articulation of the end effector 122 great than that in the device 10 of FIGS. 1-6 and 9-13.

The articulator element can be configured to be moved proximally and distally relative to the shaft 120 to articulate the end effector 122, similar to that discussed above regarding the articulator element of the device 10. When the end effector 122 is in a first configuration in which the end effector 122 is longitudinally aligned with or linear relative to the shaft 120, the articulator element can be pushed distally to pivot the distal link 136 about the second pivot point 138 and about a third pivot point 140 and to pivot the end effector 122 about a first pivot point 126 and the third pivot point 140. When the end effector 122 has pivoted such that the end effector's longitudinal axis 122 and the shaft's longitudinal axis 120A are perpendicular, the articulator element can still be pushed distally, as shown in FIG. 14, with the distal link 136 being configured to "flip" with its proximal end flipping to a distal position. In other words, the distal link's distal end can pivot about the third pivot point 140 as the proximal link 134 pushes the distal link's proximal end distally to pivot the distal link's proximal end about the second pivot point 138 and move the distal link's proximal end toward a distal-most position. Such "flipping" can allow the end effector 122 to be angularly oriented beyond 90°. The end effector 122 can also be configured to move from the first configuration to a second configuration in which the end effector 122 is angularly oriented relative to the shaft 120 by pulling the articulator element. In this illustrated embodiment, pulling the articulator element can pivot the end effector 122 about the first and third pivot points 126, 140 in an opposite direction than pushing the articulator element, with the end effector 122 being configured to angle beyond 45°, e.g., up to about 60°, in response to the proximal movement of the articulator element. In other words, the end effector 122 can be configured to pivot beyond 45° in both clockwise and counterclockwise directions relative to the shaft 20, and more particularly, can be configured to pivot up to about 130° in one of the clockwise and counterclockwise directions and to pivot up to about 60° in the other one of the clockwise and counterclockwise directions.

Figure 15:
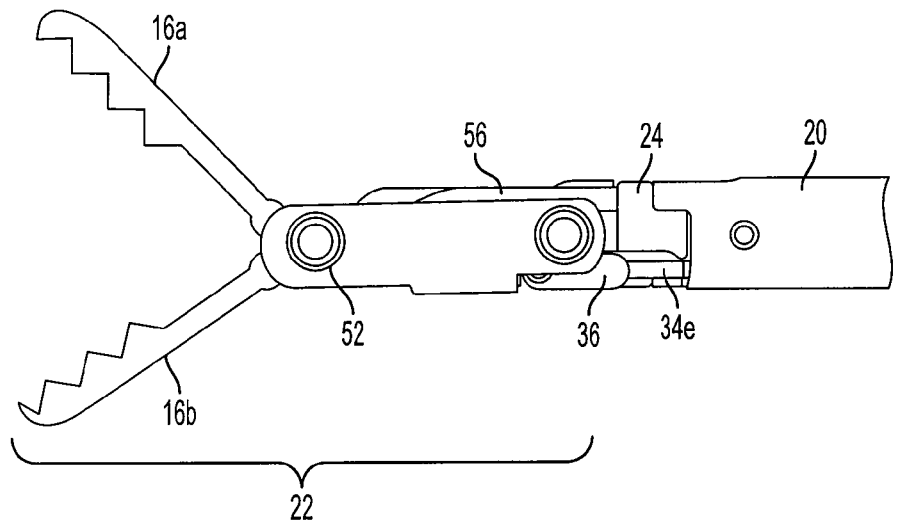
FIG. 15 is a side view of the distal portion of the device of FIG. 4 showing the end effector with its jaws in an open position.

Referring again to the embodiment illustrated in FIGS. 1-6 and 9-13, as mentioned above, the device 10 can include an actuator element configured to actuate the end effector 22, regardless of whether the end effector 22 is in the first configuration or the second configuration. The actuator element can have a variety of configurations, but in the illustrated embodiment, the actuator element extends between the handle 12 and the end effector 22 and is configured to move relative thereto to actuate the end effector 22. Generally, as shown in FIGS. 2 and 15, the actuator element can be configured such that selective movement of the actuator element relative to the shaft 20 can cause the end effector 22 to pivot the jaws 16a, 16b about a fourth pivot point 52 to selectively open and close the jaws 16a, 16b. As further discussed below, the actuator element can be configured to have a least a portion along its longitudinal length that changes in stiffness during actuation of the end effector 22, which can help facilitate actuation of the end effector 22, particularly when the end effector 22 is articulated relative to the shaft 20.

As shown in FIGS. 2-6, 9, 10, and 15, the actuator element can be a multi-bar system including a proximal rigid actuator bar, link, or rod 54, generally referred to as a "proximal link," extending through the shaft 20 and a distal flexible actuator bar, link, or rod 56, generally referred to as a "distal link." The proximal and distal links 54, 56 can each have a variety of sizes, shapes, and configurations. As mentioned above, and as shown in FIGS. 2, 5, and 6, at least a portion of the actuator element, e.g., the proximal link 56, can extend through the shaft 20 within a cannulated interior of the articulator element, e.g., within an inner passageway of the articulator element's proximal link 34. In this way, manipulation of the trigger 58 can allow the actuator element to longitudinally, slidably move within the shaft 20, relative to the shaft 20, to actuate the end effector 22 regardless of the relative position of the articulator element, e.g., regardless of the end effector's angle relative to the shaft's axis 20A.

The distal link 56 can have a diameter less than a diameter of the proximal link 54, which can allow the distal link's longitudinal axis 56A to be laterally or radially offset from the proximal link's central longitudinal axis 54A as well as laterally or radially offset from the shaft's central longitudinal axis 20A. In other words, at least a distal portion of the actuator element can have a reduced diameter region, thereby allowing a distal portion of the actuator element, e.g., the distal link 56, to be disposed parallel to the distal portion of the articulator element, e.g., the extension rod 34e, such that their axes 34A, 56A can be parallel to one another on opposite sides of the shaft's lumen 18. A person skilled in the art will appreciate that while the actuator element extends at least partially through the shaft's inner lumen 18 in the illustrated embodiment, at least a portion of the actuator element can be disposed outside the shaft 20, e.g., be slidably movable within a channel formed in an exterior surface of the shaft 20. Similarly, a person skilled in the art will also appreciate that while the actuator element extends at least partially through a channel formed in an exterior surface of the coupler 24 in the illustrated embodiment, at least a portion of the actuator element can be disposed inside the coupler 24, e.g., be slidably movable within an inner lumen of the coupler 24. Furthermore, a person skilled in the art will appreciate that a surgical device can include an actuator element including the proximal and distal links 54, 56 and an articulator element different from the one including the proximal and distal links 34, 36, and vice versa with a device including the illustrated articulator element but a different actuator element.

The proximal and distal links 54, 56 can be solid or can have one or more hollow portions, same or different from one another. As in the illustrated embodiment, the proximal and distal links 54, 56 can each be solid, with at least a distal portion of the actuator element, e.g., the distal link 56, being formed of a composite material. The composite material can allow the distal link 56 to be flexible such that it can bend near the first pivot point 26 when the end effector 22 articulates about the first pivot point 26, while also allowing the distal link 56 to be strong enough to cause opening and closing of the jaws 16a, 16b. As will be appreciated by a person skilled in the art, a composite material generally includes a material made from at least two different component materials that are physically but not chemically combined such that the different component materials can be distinguishable in the composite material and can maintain their particular properties as part of the composite material. The distal link 56 can be formed of any two or more materials combined to form a composite material.

Figure 16:
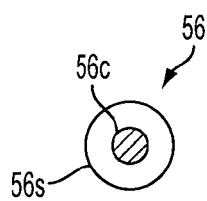
FIG. 16 is a cross-sectional view of an actuator element of the device of FIG. 1.

As in the illustrated embodiment, as shown in FIG. 16, the distal link 56 can include a core 56c surrounded by an outer sheath 56s. The core 56c and the sheath 56s each are shown in the illustrated embodiment as being substantially cylindrical with circular cross-sections, but as will be appreciated by a person skilled in the art, they can have any shape, same or different from one another. The core 56c can be formed of a first material and the sheath 56s can be formed of a second material having a greater flexibility than a flexibility of the first material such that the distal link 56 can be formed of a composite material including the first and second materials. In this way, the sheath 56s can facilitate flexing of the distal link 56 without buckling while the core 56c can provide the distal link 56 with stability, which can facilitate the distal link's longitudinal movement relative to the shaft 20 and can help force opening and closing of the jaws 16a, 16b, as discussed further below. Although the first and second materials can include any materials as appropriate for a particular surgical device, the first material can include a metal, e.g., titanium, a shape memory material such as Nitinol, stainless steel, etc., and the second material can include, e.g., a plastic such as polypropylene or polyethylene, an elastomer, etc. The distal link 56 can be formed in any way, such as by molding the sheath 56s around the core 56c. The relative sizes of the sheath 56s and the core 56c can vary, but in an exemplary embodiment, the core 56c has a relatively small cross-sectional diameter relative to the sheath 56s to provide strength to the distal link 56 while still allowing bending of the distal link 56 when the end effector 22 is in an angled position relative to the shaft's axis 20A.

The proximal link 54 can also include a solid member as in the illustrated embodiment, and can have a longitudinal length that allows it to extend from the handle 12, through the shaft 20, and distally beyond the distal end of the shaft 20 at least when the end effector 22 is articulated. A proximal end of the proximal link 54 can be operatively coupled to a thumb trigger 58 at the handle 12, illustrated in FIGS. 5 and 6 and discussed further below. Although in the illustrated embodiment the proximal link 54 extends from the handle 12 to the distal link 56, in some embodiments, an additional rigid rod can couple to the proximal link's proximal end and extend from the proximal link's proximal end to the handle 12. Furthermore, as will be appreciated by a person skilled in the art, the additional rigid rod can include multiple rigid rods. A distal end of the proximal link 54 can be coupled to a proximal end of the distal link 54, as shown in FIG. 3. The cross-sectional view of the distal portion of the device 10 in FIG. 4 may appear to indicate that the proximal end of the distal link 56 is coupled to the distal end of the articulator element's elongate tubular body 34b rather than to the actuator element's proximal link 54, but that is merely because of where the device 10 is cross-sectioned in FIG. 2. A distal end of the distal link 56 can be coupled to proximal ends of the jaws 16a, 16b, as shown in FIGS. 2 and 3.

When the end effector 22 is in the first configuration, e.g., the end effector's longitudinal axis 22A is co-axial or parallel to the shaft's longitudinal axis 20A, the actuator element can be in a corresponding straight configuration in which a longitudinal axis thereof is co-axial or parallel to the shaft's longitudinal axis 20A. In other words, when the end effector 22 is unarticulated, longitudinal axes 54A, 56A of the proximal and distal links 54, 56, respectively, can be parallel to each other and co-axial or parallel to the shaft's longitudinal axis 20A, as shown in FIG. 2. With the end effector 22 in the second, articulated configuration, the axes 22A, 56A of the end effector 22 and the distal link 56 can intersect the longitudinal axes 20A, 54A of the shaft 20 and the proximal link 54.

In response to selective movement of the trigger 58, the proximal link 54 can be configured to move longitudinally along its longitudinal axis 54A co-axial or parallel to the shaft's longitudinal axis 20A in both proximal and distal directions. A person skilled in the art will appreciate that as an alternative to the trigger 58, other types of controls, e.g., a lever, a knob, a button, a spring mechanism, etc., can be included with the handle 12 for applying a longitudinal force to the proximal link 54 co-axial or parallel to the shaft axis 20A to actuate the end effector 22. Longitudinal movement of the proximal link 54 can be configured to impart force or motion to the distal link 56, thereby imparting force or motion to the jaws 16a, 16b to cause the jaws 16a, 16b of the end effector 22 to pivot about the fourth pivot point 52. A person skilled in the art will appreciate that the force imparted from the proximal link 54 to the distal link 56 and from the distal link 56 to the jaws 16a, 16b can be simultaneous despite the presence of minimal delays as forces translate along the actuator element. Longitudinal movement of the proximal link 54 along its axis 54A can cause the distal link 56 to move longitudinally along the distal link's axis 56A, which can be straight if the end effector 22 is not articulated or can be along a bend or arc at the first pivot point 26 if the end effector 22 is articulated. In other words, movement of the proximal link 54 can be fixed along its longitudinal 54, while the distal link 56 can be configured to curve or bend relative to the proximal link 54 and to the shaft 20.

Generally, pushing the actuator element distally relative to the shaft 20 can cause the end effector's jaws 16a, 16b to move from a closed position to an open position such that the jaws 16a, 16b are angled at a non-zero angle from the end effector's longitudinal axis 22A, as shown in FIG. 15. Similarly, when the jaws 16a, 16b are in an open position, pulling the actuator element proximally relative to the shaft 20 can move the jaws 16a, 16b from the open position to the closed position. The actuator element can also be moved proximally and/or distally relative to the shaft 20 to move the jaws 16a, 16b from one open position to another open position, e.g., between different non-zero angles relative to the end effector's axis 22A.

The device 10 can optionally include a lock mechanism configured to fixedly hold the jaws 16a, 16b in the open position at a selected angular orientation. As will be appreciated by a person skill in the art, the lock mechanism can have a variety of configurations, such as a toothed rack and pawl, a depressible button configured to engage any one of a plurality of holes, etc. The degree of the jaws' opening can be varied by varying the pulling/pushing force on the actuator element.

As mentioned above, the actuator element can be flexible and can change in stiffness during actuation, e.g., the actuator's elastic modulus can be lowered during actuation. As in the illustrated embodiment, the sheath 56s of the distal link 56 can be configured to compress longitudinally when the proximal link 54 is pushed to move tips of the jaws 16a, 16b farther apart, and to expand longitudinally when the proximal link 54 is pulled to move tips of the jaws 16a, 16b closer together. In this way, the actuator element can be configured to bend around the first pivot point 26 but have sufficient strength to push/pull the jaws 16a, 16b open/closed.

Figure 17A:
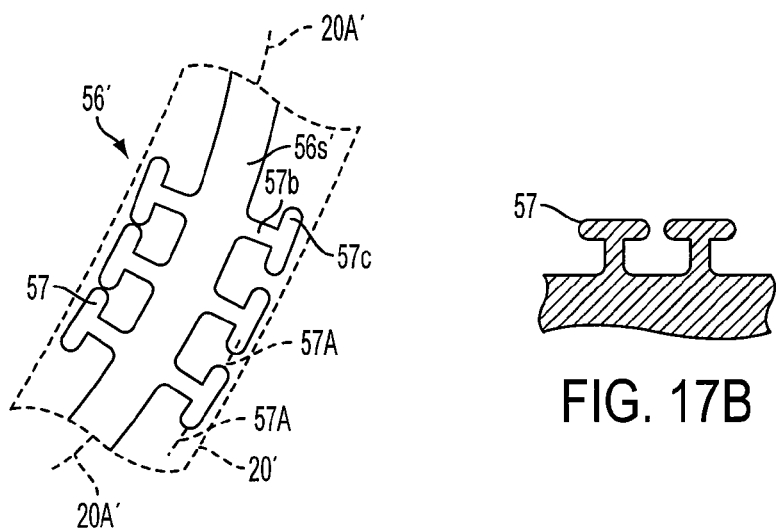
FIG. 17A is a top view of another embodiment of an actuator element having a plurality of T-shaped ribs showing the actuator element in a bent configuration.
Figure 17B:
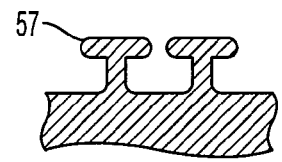
FIG. 17B is side, partial view of the actuator element of FIG. 17A showing the actuator element in a bent configuration.
Figure 17C:
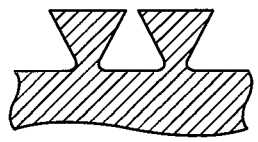
FIG. 17C is a side partial view of another embodiment of an actuator element having a plurality of triangular-shaped ribs.
Figure 17D:
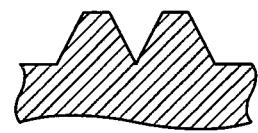
FIG. 17D is a side partial view of another embodiment of an actuator element having a plurality of truncated V-shaped ribs.

In another embodiment, illustrated in FIGS. 17A and 17B, a distal portion of an actuator element, e.g., a flexible distal link 56' extending distally from a rigid proximal link (not shown), can have a fishbone shape in which the distal link 56' includes a plurality of features configured to reduce buckling, e.g., a plurality of laterally or radially extending teeth or ribs 57, generally referred to as "ribs." The actuator element can include a core (not shown) made of a first material surrounded by an outer sheath 56s' that includes the ribs 57, the sheath 56s' including the ribs 57 being made of a second material having a greater flexibility than the first material. Although the illustrated distal link 56' includes a same number of ribs 57 extending from opposite sides of the distal link 56', a person skilled in the art will appreciate that the distal link 56' can include any number of ribs 57 arranged anywhere around the distal link 56'. The ribs 57 can have any size, shape, and configuration. As in the illustrated embodiment, the ribs 57 can have a T-shape, with a base 57b of the "T" pointing laterally or radially inward toward the core. In other embodiments, the ribs can have, e.g., a triangular shape as illustrated in FIG. 17C, a V-shape, a truncated V-shape as illustrated in FIG. 17D, an 1-shape, etc. As in the illustrated embodiment, top "T" portions or crossbars 57c of the ribs 57 can have longitudinal axes 57A parallel to a longitudinal axis 20A' of a shaft 20' at least when an end effector (not shown) at a distal end of the shaft 20' is not articulated. In this way, when the distal link 56' is bent from an unbent configuration as shown in FIG. 17B, such as when the end effector is articulated, the crossbars 57c of the ribs 57 can be configured to move closer to one another on one side of the distal link 56', e.g., the left side as in FIG. 17A, and to move apart from one another on the opposite side of the distal link 56', e.g., the right side as in FIG. 17A. Upon sufficient bending, the crossbars 57c of the ribs 57 can contact or abut one another, as also shown on the left side of FIG. 17A. In this way, the fishbone shape of the distal link 56' can help facilitate bending of the actuator element at an angle beyond 45° without buckling while also allowing the actuator element to have sufficient strength, e.g., via the core and/or movement of the ribs 57 toward one another such that adjacent crossbars 57c contact with one another, to move the jaws 16a, 16b open and closed whether the end effector is articulated or not. The distal link 56' can be similarly unbent, with adjacent crossbars 57c on either side of the distal link 56' moving closer together or father apart from one another to move the distal link 56' toward a linear or straight configuration.

Figure 17E:
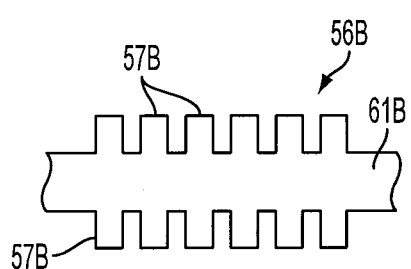
FIG. 17E is a top view of another embodiment of an actuator element having a plurality of semicircular ribs showing the actuator element in an unbent configuration.
Figure 17F:
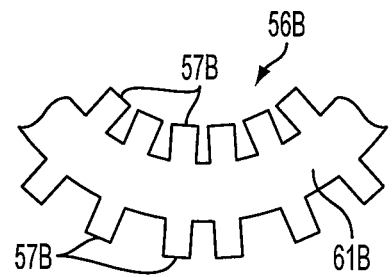
FIG. 17F is a top view of the actuator element of FIG. 17E showing the actuator element in a bent configuration.
Figure 17G:
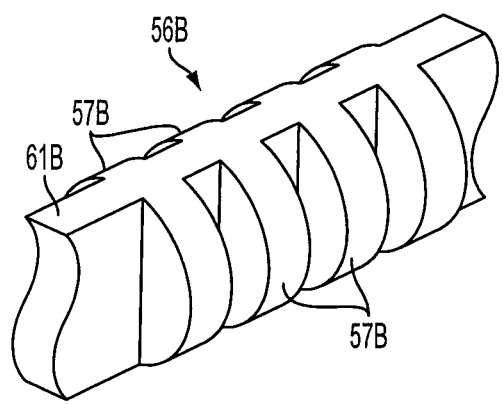
FIG. 17G is a perspective view of the actuator element of FIG. 17E.

FIGS. 17E-17G illustrate another embodiment of an actuator element including a distal portion, e.g., a flexible distal link 56B, having a fishbone shape. In this illustrated embodiment, the distal link 56B includes a plurality of half-moon or semicircular ribs 57B extending laterally or radially from a central portion 61B thereof. When the distal link 57B moves from an unbent configuration, shown in FIGS. 17E and 17G, to a bent configuration, shown in FIG. 17F, the ribs 57B can move similar to that discussed above regarding the distal link 56' of FIG. 17A with ribs 57B on one side of the distal link 56B moving closer to one another while ribs 57B on the other side move apart from one another.

Figure 18:
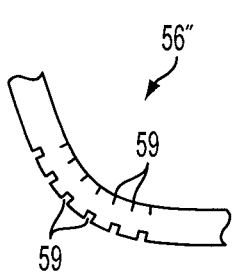
FIG. 18 is a top view of another embodiment of an actuator element having a plurality of slits.

In another embodiment, illustrated in FIG. 18, a distal portion of an actuator element, e.g., a flexible distal link 56" extending distally from a rigid proximal link (not shown), can have a fishbone shape in which the distal link 56" includes a plurality of features to reduce buckling in the form of cuts or slits 59, generally referred to as "slits," formed therein. The slits 59 can generally be configured similar to the ribs 57 discussed above, e.g., be formed in an outer sheath of the distal link 56" on opposite sides thereof. When the distal link 56" bends to accommodate articulation of the end effector (not shown), the slits 59 can compress together, e.g., as shown on the right in FIG. 18, and expand apart, e.g., as shown on the left in FIG. 18, as necessary to facilitate bending of the distal link 56" and facilitate actuation of the end effector. If the slits 59 are of sufficient size and shape, pushing and pulling the actuator element can change a diameter of the distal link 56", with the distal link 56" increasing in diameter when pushed, e.g., as the slits 59 compress, and decreasing in diameter when pulled, e.g., as the slits 59 move apart from one another.

In another embodiment, the actuator element can include at least one cable, e.g., a braided cable. As will be appreciated by a person skilled in the art, the cable can be configured to be actuated from the handle 12 to actuate the end effector 22. Exemplary embodiments of cables configured to actuate an end effector are described in more detail in U.S. Patent Publication No. 2008/0147113 filed Dec. 14, 2006 entitled "Manually Articulating Devices," which is hereby incorporated by reference in its entirety.

Referring again to the embodiment of FIGS. 1-6, as will be appreciated by a person skilled in the art, the handle 12 can include a rotating mechanism configured to rotate the shaft 20, such as a knob 60 as shown in FIGS. 5 and 6, a lever, a wired or wireless electronic control, etc. The knob 60 can be configured to rotate the shaft 20 360° clockwise and/or counterclockwise about the shaft's longitudinal axis 20A. Rotation of the shaft 20 about its axis 20A can also rotate the end effector 22 about the shaft's axis 20A. The shaft 20 can be rotated when the end effector 22 in either the straight configuration or the articulated configuration to further increase the positioning range of the end effector 22.

Figure 19:
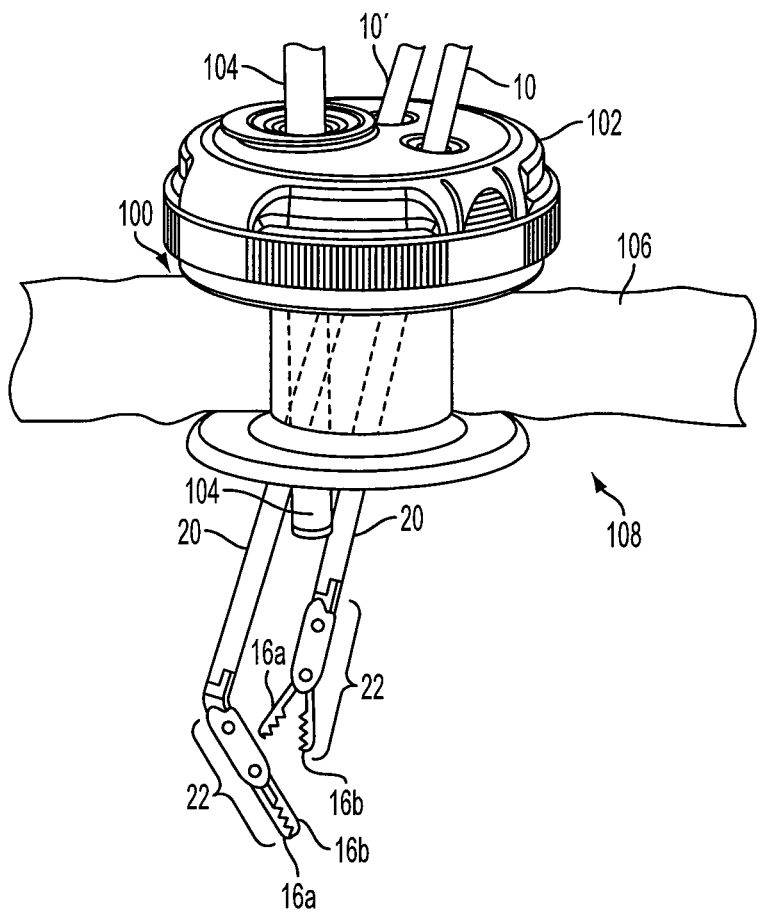
FIG. 19 is a perspective, partially cross-sectional view of a surgical access device positioned within a tissue opening and having first and second laparoscopic devices and a scoping device inserted therethrough and positioned within a body cavity, the first laparoscopic device having an end effector in an articulated configuration, and the second laparoscopic device having an end effector in a straight configuration.

In use, as shown in an exemplary embodiment in FIG. 19, one or more surgical devices 10 can be inserted through an opening 100 in tissue 106 to access a body cavity 108 underlying the tissue 106 where the devices 10 can perform any type of surgical procedure. Although the illustrated devices 10 are each those of FIG. 1, a person skilled in the art will appreciate that any one or more devices can be inserted into the body cavity 108. As mentioned above, a person skilled in the art will also appreciate that while the devices 10 are shown in the illustrated embodiment in use in a laparoscopic procedure and inserted into the body cavity 108, e.g., the abdominal cavity, through a multiple port access device 102 positioned in the tissue opening 100, e.g., an incision at the navel, any of the surgical devices disclosed herein can be used in a variety of surgical procedures and inserted into a patient's body in any number of ways. Prior to insertion of any instruments through the multiple port access device 102, insufflation can be provided through an insufflation port, as will be appreciated by a person skilled in the art. A scoping device 104 can also be inserted through the multiple port access device 102 to provide visualization. Non-limiting examples of a scoping device include an endoscope, a laparoscope, and a colonoscope.

The multiple port access device 102 can include multiple instrument openings each configured to receive an instrument inserted therethrough. Each opening can have an associated sealing port that can be configured to provide at least one instrument seal that forms a seal around an instrument disposed therethrough, but otherwise does not form a seal when no instrument is disposed therethrough, at least one channel seal or zero-closure seal that seals a working channel created by the sealing port when no instrument is disposed therethrough, or a combination instrument seal and channel seal that is effective to both form a seal around an instrument disposed therethrough and to form a seal in the working channel when no instrument is disposed therethrough. Exemplary embodiments of multiple port access devices are described in more detail in U.S. patent application Ser. No. 12/399,482 filed Mar. 6, 2009 entitled "Methods And Devices For Providing Access Into A Body Cavity," U.S. patent application Ser. No. 12/399,473 filed Mar. 6, 2009 entitled "Methods And Devices For Providing Access Into A Body Cavity," U.S. patent application Ser. No. 12/512,542 filed Jul. 30, 2009 entitled "Methods And Devices For Providing Access Into A Body Cavity," U.S. patent application Ser. No. 12/512,568 filed Jul. 30, 2009 entitled "Methods And Devices For Providing Access Into A Body Cavity," U.S. patent application Ser. No. 12/399,633 filed Mar. 6, 2009 entitled "Methods And Devices For Providing Access Into A Body Cavity," U.S. patent application Ser. No. 12/399,625 filed Mar. 6, 2009 entitled "Methods And Devices For Providing Access Into A Body Cavity," U.S. patent application Ser. No. 12/399,547 filed Mar. 6, 2009 entitled "Surgical Access Devices And Methods Providing Seal Movement In Predefined Paths," U.S. patent application Ser. No. 12/399,656 filed Mar. 6, 2009 entitled "Surgical Access Devices And Methods Providing Seal Movement In Predefined Movement Regions," and U.S. patent application Ser. No. 12/766,086 filed Apr. 23, 2010 entitled "Methods And Devices For Accessing A Body Cavity," which are hereby incorporated by reference in their entireties.

Figure 20:
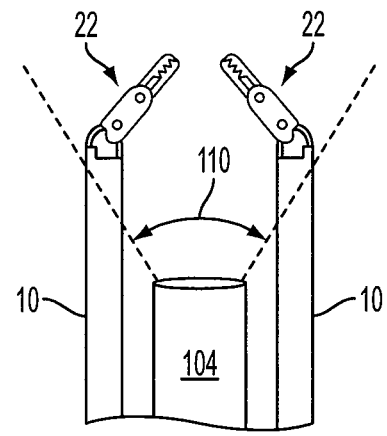
FIG. 20 is a side view of distal portions of the laparoscopic devices and the scoping device of FIG. 19 positioned in the body cavity, the end effectors each being in an articulated configuration.

The devices 10 can be simultaneously or sequentially inserted through the multiple port access device 102 with the end effectors 22 in straight configurations to position distal portions of the shafts 20 within the body cavity 108. The shafts 20 inserted through the multiple port access device 102 can each extend generally parallel to one another, e.g., have parallel longitudinal axes. After distal portions of the shafts 20 have been positioned within the body cavity 108, the handles 12 of the devices 10 can be manipulated, simultaneously or sequentially, to move the end effectors 22 from straight configurations to articulated configurations to allow the end effectors 22 at respective distal ends of the shafts 20 to be brought together in a non-interfering, cooperative, facing relationship and to be within a viewing range 110 of the scoping device 104, as also illustrated in FIG. 20. The end effectors 22 can be articulated any amount, including not at all, same or different from one another, and can be selectively adjusted during the surgical procedure to articulate more or less as desired. Because the end effectors 22 can articulate beyond 45°, the end effectors 22 can be configured to angle toward a target tissue and/or another device from a variety of relative positions, e.g., from above, from a side position, or from below. The shafts 20 can also be rotated relative to the handles 12, and the end effectors' jaws 16a, 16b can be opened and closed. The devices 10 can thus allow the shafts 20 to be easily inserted into a body in straight configurations through a single, relatively small opening 100 with the shafts 20' being substantially parallel, and the end effectors 22 can be subsequently articulated to optimally position the end effectors 22 relative to the surgical site, to each other, to the scoping device 104, and to any other tools within the body cavity 108. Because the device 10 can be articulated, its end effector 22 can be positioned at an angle with respect to a remainder of the shaft 20 thereof, positioning of the device and visualization of the device and the surgical site can be improved. In other words, even though the devices 10 and the scoping device 104 are inserted through a common incision, it is still possible to see the end effectors 22 of the devices 10' and to bring the end effectors 22 of the two instruments devices 10 together in a facing relationship at a single point within the body cavity 108.

The shafts 20 can also be easily removed from the patient's body with the end effectors 22 unarticulated, first moving the end effectors 22 from articulated configurations to straight configurations if necessary. The multiple port access device 102 can be configured to allow further adjustment of instruments inserted therethrough, such as by allowing collective rotation of the instruments around a central axis of the multiple port access device 102.

A proximal housing portion of the multiple port access device 102 can be configured to be removable from a distal retractor portion of the multiple port access device 102. Thus, at any point before, during, or after a surgical procedure, the proximal housing portion can in full or part be released from the distal retractor portion, and the distal retractor portion can be removed from the tissue 106. With the proximal housing portion of the multiple port access device 102 disengaged from the distal retractor portion and with the distal retractor portion still positioned in the tissue opening 100, a working channel of the distal retractor portion can provide access to the body cavity 108 underlying the tissue 106. One or more of the devices 10 and/or other surgical instruments can be advanced through the working channel, such as a waste removal bag configured to hold waste material, e.g., dissected tissue, excess fluid, etc., from the body cavity 108. The bag can be introduced into the body cavity 108 through the distal retractor portion's working channel or other access port. A person skilled in the art will appreciate that one or more surgical instruments can be advanced through the distal retractor portion's working channel before and/or after the proximal housing portion has been attached to the distal retractor portion. A surgical drape can optionally be placed over the distal retractor portion and the tissue opening 100 during removal of the distal retractor portion to help reduce dispersion of bodily fluid outside the surgical space.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., a handle, a proximal housing portion of a surgical access device, an end effector, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A laparoscopic device, comprising:
    an elongate shaft having proximal and distal ends defining a longitudinal axis extending therebetween, the elongate shaft having an inner lumen extending therethrough between the proximal and distal ends;
    an end effector coupled to the distal end of the elongate shaft; and
    an actuator element coupled to the end effector and extending between the proximal and distal ends of the elongate shaft along the longitudinal axis through the inner lumen, a proximal portion of the actuator element being rigid and a distal portion of the actuator element being flexible, the distal portion formed of a composite material including a solid core formed of a first material and an outer sheath formed of a second material having a greater flexibility than the first material, the outer sheath surrounding the solid core and being non-slidable relative thereto;
    wherein the actuator element is movable relative to the elongate shaft to actuate the end effector, and
    wherein the outer sheath includes a plurality of features extending therefrom and disposed in the elongate shaft, the plurality of features changing a stiffness of the actuator element when the actuator element is flexed.

2. The device of claim 1, wherein the first material comprises a metal and the second material comprises a plastic.

3. The device of claim 1, wherein the distal portion has a stiffness that is configured to change during the actuation of the end effector.

4. The device of claim 1, further comprising an articulator element coupled to the end effector and extending through the inner lumen of the elongate shaft between the proximal and distal ends of the elongate shaft, the articulator element being configured to articulate the end effector to angularly orient the end effector relative to the longitudinal axis of the elongate shaft.

5. The device of claim 4, wherein the articulator element extends through the inner lumen on one side of the inner lumen, and the actuator element extends through the inner lumen on an opposite side of the inner lumen.

6. A laparoscopic device, comprising:
    a cannulated elongate shaft having proximal and distal ends defining a longitudinal axis extending therebetween;
    an end effector coupled to the distal end of the shaft; and
    an actuator element coupled to the end effector and extending through the cannulated elongate shaft, the actuator element including a rigid proximal portion and a flexible distal portion, the actuator element being formed of a composite material including a sheath surrounding a central core;
    wherein the actuator element is movable relative to the cannulated elongate shaft to actuate the end effector, and
    wherein the sheath has a plurality of features extending therefrom and disposed in the cannulated elongate shaft, the plurality of features changing a stiffness of the actuator element when the actuator element is flexed.

7. The device of claim 6, wherein the central core is formed of a metal, and the sheath is formed of a plastic.

8. The device of claim 6, wherein the plurality of features include a plurality of ribs extending radially outward from the central core.

9. The device of claim 8, wherein the plurality of ribs are configured to compress together to increase the stiffness of the actuator element when the actuator element moves to actuate the end effector.

10. The device of claim 8, wherein each of the plurality of ribs include a base portion that is substantially perpendicular to a longitudinal axis of the core and a cross bar portion that is coupled to the base portion and is substantially parallel to the longitudinal axis of the core.

11. The device of claim 10, wherein when the actuator element is not flexed, the cross bar portions of the plurality of ribs are not in contact and when the actuator element is flexed, the cross bar portions of at least two adjacent ribs of the plurality of ribs are in contact.

12. The device of claim 8, wherein each of the plurality of ribs include a base portion extending radially away from the core and a cross bar portion that is oriented substantially perpendicular to the base portion.

13. The device of claim 8, wherein each of the plurality of ribs are substantially T-shaped.

14. The device of claim 6, wherein the actuator element comprises:
   a rigid actuator member extending through the cannulated elongate shaft; and
   a flexible actuator member having a proximal end coupled to a distal end of the rigid actuator member, and having a distal end coupled to the end effector, the flexible actuator member being formed of a composite material;
   wherein the rigid actuator member is configured to translate longitudinally through the cannulated elongate shaft to move the flexible actuator member relative to the cannulated elongate shaft and to change the stiffness of the flexible actuator member to actuate the end effector.

15. The device of claim 6, further comprising an articulator element extending through the cannulated elongate shaft along the longitudinal axis, the articulator element being configured to articulate the end effector at an angle relative to the longitudinal axis of the cannulated elongate shaft.

16. The device of claim 15, wherein the articulator element extends through the cannulated elongate shaft along one side thereof, and the actuator element extends through the cannulated elongate shaft along an opposite side thereof.

* * * * *